United States Patent [19]
Burton et al.

[11] Patent Number: 5,652,348
[45] Date of Patent: Jul. 29, 1997

[54] CHROMATOGRAPHIC RESINS AND METHODS FOR USING SAME

[75] Inventors: Simon C. Burton; Neill Ward Haggarty; David R. K. Harding, all of Palmerston North, New Zealand; Nathaniel Todd Becker, Burlingame, Calif.; Ben A. Bulthuis, San Bruno, Calif.; Landon M. Steele, San Francisco, Calif.

[73] Assignee: Massey University, Palmerston North, New Zealand

[21] Appl. No.: 311,100

[22] Filed: Sep. 23, 1994

[51] Int. Cl.[6] ................................ C08B 37/08
[52] U.S. Cl. ................ 536/20; 536/22.1; 536/25.4; 536/25.41
[58] Field of Search ................ 536/20, 22.1, 25.4, 536/25.41

[56] References Cited

U.S. PATENT DOCUMENTS

| | | |
|---|---|---|
| 3,917,527 | 11/1975 | Shaltiel . |
| 3,956,179 | 5/1976 | Sebestian et al. . |
| 3,960,720 | 6/1976 | Porath et al. . |
| 4,048,416 | 9/1977 | Axen et al. . |
| 4,886,755 | 12/1989 | Ngo . |
| 4,981,961 | 1/1991 | Ngo . |

FOREIGN PATENT DOCUMENTS

| | | |
|---|---|---|
| 0 172 579 | 2/1986 | European Pat. Off. . |
| 0 180 563 | 5/1986 | European Pat. Off. . |
| 1 180 564 | 7/1986 | European Pat. Off. . |
| 0 337 144 | 3/1989 | European Pat. Off. . |
| 2 644 474 | 1/1990 | France . |
| 3605908 | 2/1985 | Germany . |
| 280 333 | 8/1990 | Germany . |
| 488814 | 3/1993 | Sweden . |
| WO87/02273 | 4/1987 | WIPO . |
| WO90/15865 | 12/1990 | WIPO . |
| WO94/04192 | 3/1994 | WIPO . |

OTHER PUBLICATIONS

Bischoff, et al., "Nucleic acid resolution by mixed–mode chromatography", J. Chromatogr., 296: 329–337 (1984).

Bischoff, et al., "Chemically synthesized hydrophobic anion–exchange HPLC supports used for oligonucleotide resolution by mixed mode chromatography", Journal of Chromatography 9667–9673 (1983).

McLaughlin, W., "Mixed mode chromatography of nucleic acids," Chem, Rev., 89: 309–319 (1989).

Wu, D. et al., "Effects of stationary phase liquid density on high–performance ion–exchange chromatography of proteins", Journal of Chromatography, 598:7–13 (1992).

Asenjo, J.A. et al., "Rational Design of Purification Processes for Recombinant Proteins", Ann, N.Y. Acad. Sci., 646:334–356 (1991).

Bischoff, R. et al., "Chemically Synthesized Hydrophobic Anion–Exchange High–Performance Liquid Chromatography Supports Used For Oligonucleotide Resolution By Mixed Mode Chromatography", Journal of Chromatography, 9667–9673 (1983).

Bischoff, R. et al, "Isolation of Specific tRNAs Using an Ionic–Hydrophobic Mixed–Mode Chromatographic Matrix", Analytical Biochemistry, 151:526–533 (1985).

(List continued on next page.)

Primary Examiner—James J. Seidleck
Assistant Examiner—D. Truong
Attorney, Agent, or Firm—Burns, Doane, Swecker & Mathis L.L.P.

[57] ABSTRACT

Disclosed are rationally designed mixed mode resins which are useful in recovering a target compound from an aqueous solution and methods for use of such resins. The resins described herein have a hydrophobic character at the pH of binding of the target compound and a hydrophilic and/or electrostatic character at the pH of desorption of the target compound from the resin and are specifically designed to bind the target compound from an aqueous solution at both a low and high ionic strength.

28 Claims, 5 Drawing Sheets

OTHER PUBLICATIONS

Bischoff, R. et al., "Mixed–Mode Chromatographic Matrices For the Resolution of Transfer Ribonucleic Acids", *Journal of Chromatography*, 317:251–261 (1984).

Bischoff, R., et al., "Nucleic Acid Resolution By Mixed–Mode Chromatography", *Journal of Chromatography*, (1984).

Burton, C., et al., "Efficient Substitution of 1,1' –carbonyldiimidazole Activated Cellulose and Sepharose Matrices With Amino Acyl Spacer Arms", *Journal of Chromatography*, 587:271–275 (1991).

Butler, L.G., "Enzyme Immobilization by Adsorption on Hydrophobic Derivatives of Cellulose and Other Hydrophilic Materials", *Arch. Biochem. Biophys.*, 171:645–650 (1975).

Caldwell, K.D. et al., "Utilization of Hydrophobic Interaction for the Formation of an Enzyme Reactor Bed", *Biotechnol. Bioeng.*, 17:613–616 (1975).

Cashion, P. et al., "Enzyme Immobilation on Tritylagarose", *Biotech. Bioeng.*, 24:403–423 (1982).

Champluvier, B. et al., "Dye–Ligand Membranes as Selective Adsorbents for Rapid Purification of Enzymes: A Case Study", *Biotechnol. Bioeng.*, 40:33–40 (1992).

Crowther et al., "High–Performance Liquid Chromatographic Separation of Oligonucleotides And Other Nucleic Acid Constituents On Multifunctional Stationary Phases", *Journal of Chromatography*, 282:619–628 (1983).

Floyd et al., "Use of Diluted Anion–Exchange and Hydrophobic Properties in Separating Synthetic Single–Stranded Oligodeoxyribonucleotides on Mixed–Ligand Stationary Phases", *Chromatographia*, 21:402–408 (1986).

Heath, C.A. et al., "Synthetic Membranes in Biotechnology: Realities and Possibilities", *Adv. Biochem. Eng./Biotechnol.*, 47:45–88 (1992).

Heinitz et al., "Chromatography Of Proteins On Hydrophobic Interaction And Ion–Exchange Chromatographic Matrices: Mobile Phase Contributions To Selectivity", *Journal of Chromatography*, 443:173–182 (1988).

Hoffman et al., "Ion Exchange in Reversed–Phase Chromatography Of Some Simple Organic Cations", *Journal of Chromatographic Science*, 28:428–431 (1990).

Hoftsee, B.H.J., "Protein Binding by Agarose Carrying Hydrophobic Groups in Conjunction with Charges", *Biochem. Biophys. Res. Commun.*, 50:751–757 (1973).

Hoftsee, B.H.J., "Hydrophobic Affinity Chromatography of Proteins", *Anal. Biochem.*, 52:430–448 (1973).

Hutchinson, D.W., "The Preparation and Properties of Immobilised Dipeptidyl-aminopeptidase I (cathepsin C)", *Biochem. Biophys. Acta*, 916:1–4 (1987).

Johansson, G. et al., "Affinity Partition Between Aqueous Phases—A Tool for Large–Scale Purification of Enzymes", *J. Biotechnol.*, 11:135–142 (1989).

Jost, R. et al., "The Mode of Adsorption of Proteins to Aliphatic and Aromatic Amines Coupled to Cyanogen Bromide–Activate Agarose", *Biochem. Biophys.*, 362:75–82 (1974).

Kasche V., et al., "Rapid Protein Purification Using Phenylbutylamine–Eupergit: a novel method for large–scale procedures", *J Chromatogr.*, 510:149–154 (1990).

Lloyd et al., "Mixed–Mode Coumn Thermospray Liquid Chromatography/Mass Spectrometry", *Anal. Chem.*, 59:2533–2534. (1987).

Luong, J.H.T. et al., "Synthesis and Characterization of a Water–Soluble Affinity Polymer for Trypsin Purification", *Biotechnol. Bioeng.*, 31:439–446 (1988).

Maisano et al., "Synthesis Of New Hydrophobic Adsorbents Based on Homonologues eies of Uncharged Alkyl Sulphide Agarose Derivatives", *J. Chromatagraphy*, 321:305–317 (1985).

McLaughlin, W., "Mixed–Mode Chromatography of Nucleic Acids", *Chem. Rev.*, 89:309–319 (1989).

Nau, "Effects of Mobile Phase Conditions on Protein Conformation and Chromatographic Selectivity in Ion Exchange and Hydrophobic Interactions Chromatography", *BioChromatography*, 4:62–68 (1989).

Ngo, et al., "Chemistry and Preparation of Affinity Ligands Useful in Immunoglobulin Isolation and Serum Protein Separation", *Journal of Chromatography*, 510:281–291 (1990).

Ochoa, J.L., "Hydrophobic (Interaction) Chromatography", *Biochimie*, 60:1–15 (1978).

Ortin, A. et al., "Large Scale Extraction of a $\alpha$–Lactalbumin and $\beta$–Lactoglobulin from Bovine Whey by Precipitation with Polyethylene Glycol and Partitioning in Aqueous Two–Phase Systems", *Prep. Biochem.*, 22:53–66 (1992).

Oscarsson, S. et al., "Covalent Chromatography and Salt–Promoted Thiophilic Adsorption", *Anal. Biochem.*, 176:330–337 (1989).

Porath, J. et al., "A New Kind of 'Thiophilic' Electron–Donor–Acceptor Adsorbent", *Makromol. Chem., Macromol. Symp.*, 17:359–371 (1988).

Simmonds et al., "Protein Chromatography on Adsorbents with Hydrophobic and Ionic Groups", *Biochem. J.*, 157:153–159 (1976).

Rosengren et al., "Hydrophobic Interaction Chromatography Non–Charged Sepharose Derivatives", *Biochimica et Biophysica Acta*, 412:51–61 (1975).

Ruaan, R.C. et al., "Dual–Functional Affinity Protein Purification", *Biotechnol. Prog.*, 4:107–112 (1988).

Sasaki I. et al., "Hydrophobic–Ionic Chromatography", *J. Biochem.*, 86:1537–1548 (1979).

Sasaki I. et al., "Hydrophobic–Ionic Chromatography: Its Application to Microbial and Glucose Oxidase, Hyaluronidase, Cholesterol Oxidase, and Cholesterol Esterase", *J. Biochem.*, 91:1555–1561 (1982).

Simons, P. C. et al., "Purification of Glutathione S–Transferases from Human Liver by Glutathione–Affinity Chromatography", *Anal. Biochem.*, 82:334–341 (1977).

Teichberg, V.I., "Affinity–Repulsion Chromatography", *J. Chromatogr.*, 510:49–57 (1990).

Voutsinas, P.L. et al., "Coagulation of Skim Milk with Proteases Immobilized on Hydrophobic Carriers", *Dairy Sci.*, 66:694–703 (1983).

Yon, R.J., et al., "Protein Chromatography on Adsorbents with Hydrophobic and Ionic Groups", *Biochem J.*, 151:281–290 (1975).

Yon R. J., "Chromatography of Lipophilic Proteins on Adsorbents Containing Mixed Hydrophobic and Ionic Groups", *Biochem J.*, 126:765–767 (1972).

Zhu et al., "Mixed–mode Hydrophilic and Ionic Interaction Chromatography Rivals Reversed Phase Liquid Chromatography for the Separation of Peptides", *Journal of Chromatography*, 594:75–86 (1992).

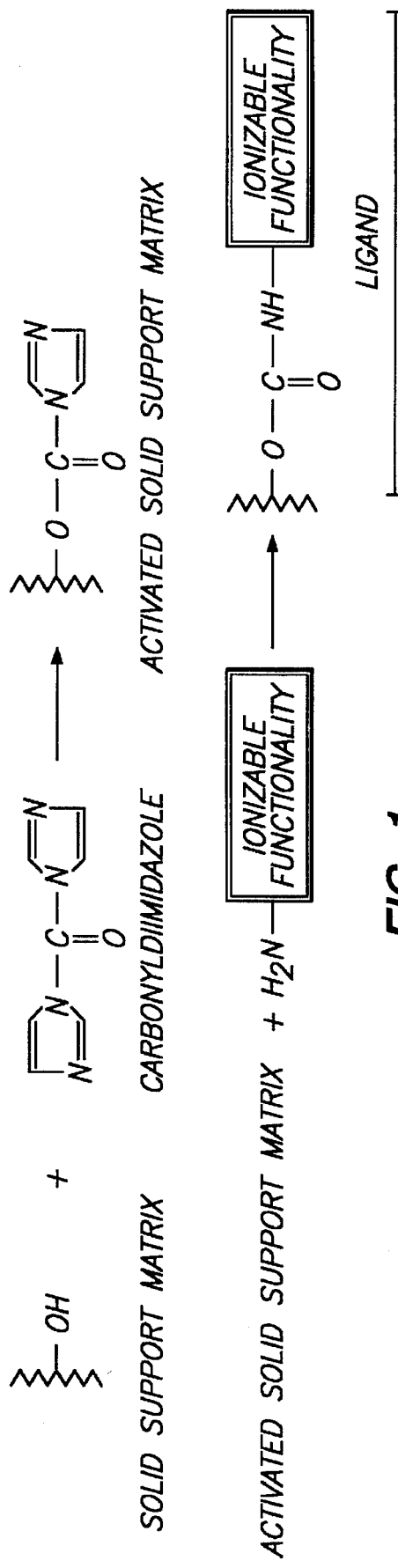
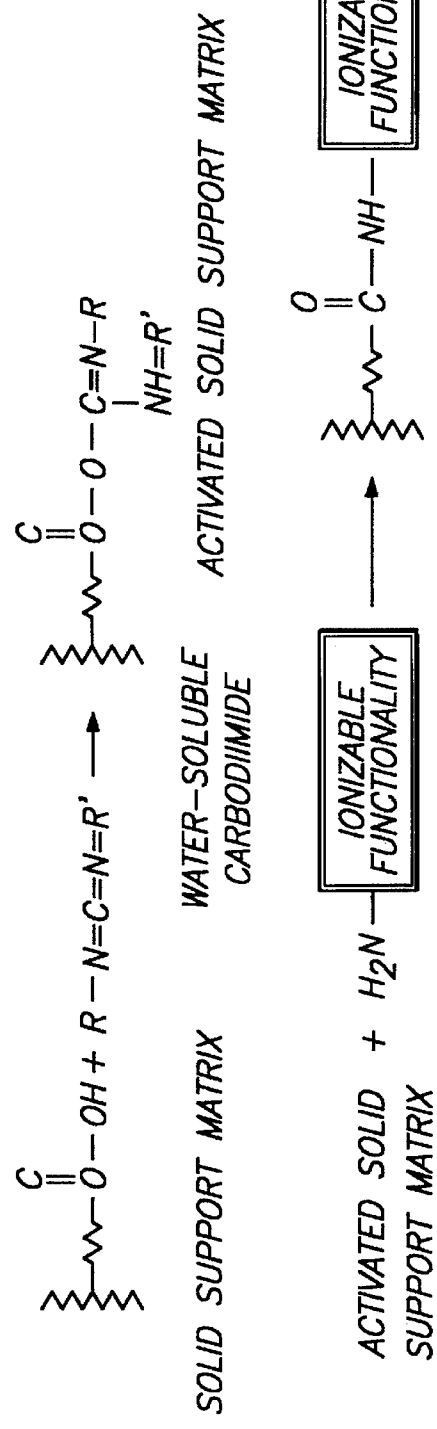
FIG. 1
FIG. 2

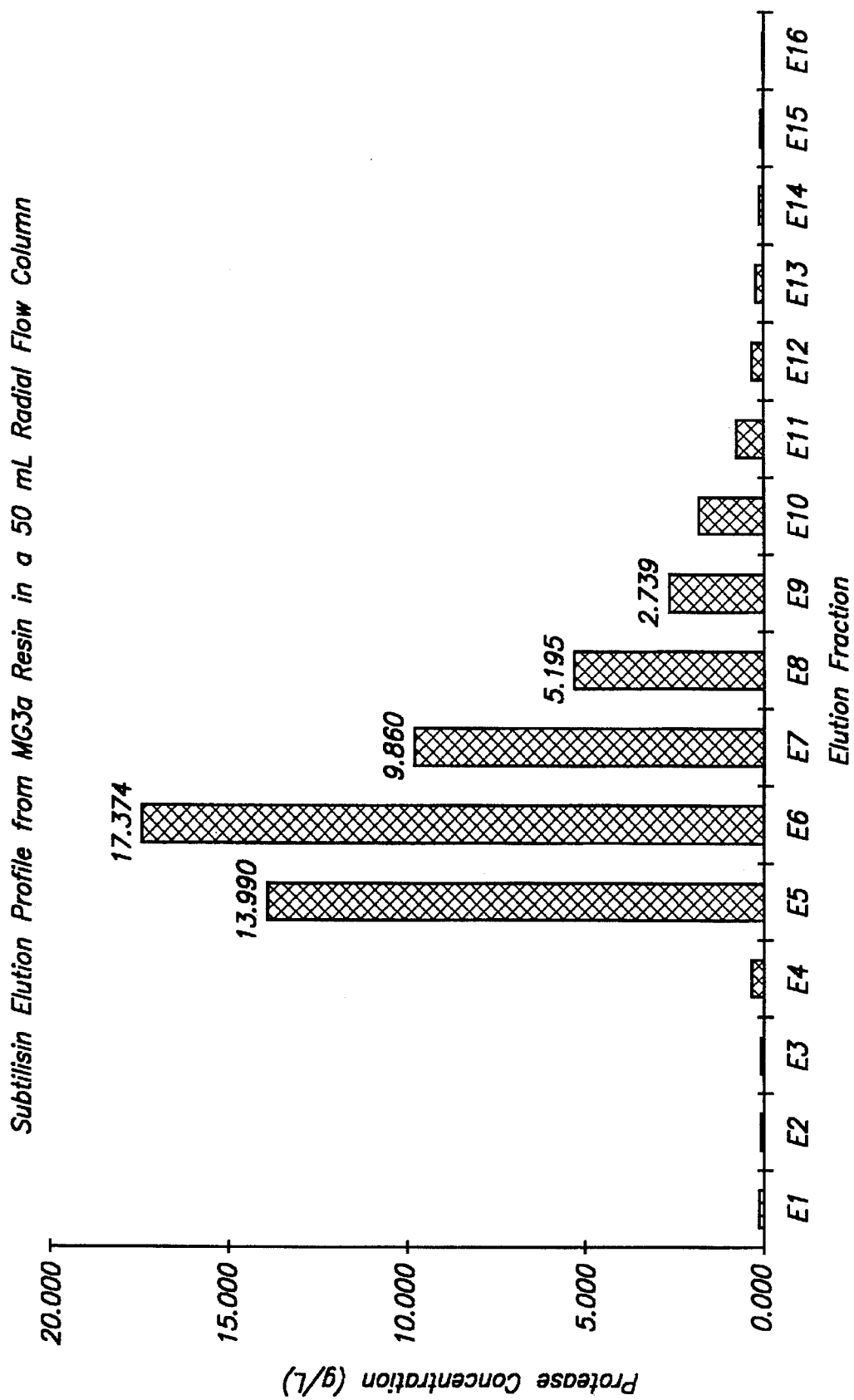

CHROMATOGRAPHIC RESINS AND METHODS FOR USING SAME

BACKGROUND OF THE INVENTION

1. Field of the Invention

This invention relates to rationally designed mixed mode resins which are useful in recovering a target compound from an aqueous solution and methods for use of such resins. The resins described herein have a hydrophobic character at the pH of binding of the target compound and a hydrophilic and/or electrostatic character at the pH of desorption of the target compound from the resin and are specifically designed to bind the target compound from an aqueous solution at both a low and high ionic strength.

2. References

The following references are referred to in the specification as numbers in []:

1 Ochoa, J. L., "Hydrophobic (interaction) chromatography", Biochimie, 60:1–15 (1978).
2 Yon, R. J., et al., "Protein Chromatography on Adsorbents with Hydrophobic and Ionic Groups", Biochem J., 151:281–290 (1975).
3 Yon, R. J., "Chromatography of Lipophilic Proteins on Adsorbents Containing Mixed Hydrophobic and Ionic Groups", Biochem J., 126:765–767 (1972).
4 Hofstee, B. H. J., "Hydrophobic Affinity Chromatography of Proteins", Anal. Biochem., 52:430–448 (1973).
5 Hofstee, B. H. J., "Protein Binding by Agarose Carrying Hydrophobic Groups in Conjunction with Charges", Biochem. Biophys. Res. Commun., 50:751–757 (1973).
6 Bischoff, et al., "Nucleic Acid Resolution by Mixed-Mode Chromatography", J. Chromatogr., 296:329–337 (1984).
7 Kasche, V., et al., "Rapid Protein Purification Using Phenylbutylamine-Eupergit: a novel method for large-scale procedures", J. Chromatogr., 510:149–154 (1990).
8 Sasaki, I. et al., "Hydrophobic-Ionic Chromatography", J. Biochem., 86:1537–1548 (1979).
9 Sasaki, I. et al., "Hydrophobic-Ionic Chromatography: Its Application to Microbial and Glucose Oxidase, Hyaluronidase, Cholesterol Oxidase, and Cholesterol Esterase", J. Biochem., 91:1555–1561 (1982).
10 Simons, P. C. et al., "Purification of Glutathione S-Transferases from Human Liver by Glutathione-Affinity Chromatography", Anal. Biochem., 82:334–341 (1977).
11 McLaughlin, "Mixed-Mode Chromatography of Nucleic Acids", Chem. Rev., 89:309–319 (1989)
12 Bischoff, et al., "Mixed-Mode Chromatographic Matrices for the Resolution of Transfer Ribonucleic Acids", J. Chromatogr., 317:251–261 (1984)
13 Champluvier, B., et al., "Dye-Ligand Membranes as Selective Adsorbents for Rapid Purification of Enzymes: A Case Study", Biotechnol. Bioeng., 40:33–40 (1992)
14 Butler, L. G., "Enzyme Immobilization by Adsorption on Hydrophobic Derivatives of Cellulose and Other Hydrophilic Materials", Arch. Biochem. Biophys., 171:645–650 (1975).
15 Caldwell, K. D., et al., "Utilization of Hydrophobic Interaction for the Formation of an Enzyme Reactor Bed", Biotechnol. Bioeng., 17:613–616 (1975).
16 Cashion, P., et al., "Enzyme Immobilization on Tritylagarose", Biotech. Bioeng., 24:403–423 (1982).
17 Voutsinas, P. L., et al., "Coagulation of Skim Milk with Proteases Immobilized on Hydrophobic Carriers", Dairy Sci., 66:694–703 (1983).
18 Hutchinson, D. W., "The Preparation and Properties of Immobilized Dipeptidyl-aminopeptidase I (cathepsin C)", Biochim. Biophys. Acta, 916:1–4 (1987).
19 Asenjo, J. A., et al., "Rational Design of Purification Processes for Recombinant Proteins", Ann. N.Y. Acad. Sci., 646:334–356 (1991)
20 Ruann, R. C., et al., "Dual-Functional Affinity Protein Purification", Biotechnol. Prog., 4:107–112 (1988)
21 Teichberg, V. I., "Affinity-Repulsion Chromatography", J. Chromatogr., 510:49–57 (1990)
22 Johansson, G., et al., "Affinity Partition Between Aqueous Phases—A Tool for Large-Scale Purification of Enzymes", J. Biotechnol., 11:135–142 (1989)
23 Ortin, A., et al., "Large Scale Extraction of α-Lactalbumin and β-Lactoglobulin from Bovine Whey by Precipitation with Polyethylene Glycol and Partitioning in Aqueous Two-Phase Systems", Prep. Biochem., 22:53–66 (1992)
24 Heath, C. A. et al., "Synthetic Membranes in Biotechnology: Realities and Possibilities", Adv. Biochem. Eng./Biotechnol., 47:45–88 (1992)
25 Luong, J. H. T., et al., "Synthesis and Characterization of a Water-Soluble Affinity Polymer for Trypsin Purification", Biotechnol. Bioeng., 31:439–446 (1988)

The disclosure of each of the above-referenced publications is hereby incorporated by reference in its entirety to the same extent as if each and every reference were individually incorporated by reference herein.

3. State of the Art

In recent years, several techniques have been developed and/or optimized to effect separation and purification of target compounds from an aqueous mixture. Separation and purification techniques heretofore employed with such compounds include, by way of example, ion-exchange chromatography, hydrophobic interaction chromatography (HIC) [1], affinity chromatography, and the like. The multiplicity of such chromatographic techniques reflect the difficulty in effecting separation and/or purification of the target compounds while minimizing the complexity of the separation/purification procedure and each of the techniques recited above suffer from one or more drawbacks limiting their broad use on an industrial scale.

Mixed mode chromatographic resins have also been employed in the art wherein such resins effect binding of a target compound under hydrophobic conditions and effect desorption of the target compound from the resin under electrostatic (ionic) or hydrophilic conditions. Examples of such mixed mode resins are found in Kasche, et al. [7], Bischoff, et al. [6], McLaughlin [11] and Bischoff, et al. [12].

One problem typical of mixed mode chromatographic resins of the prior art is that binding efficiencies of less hydrophobic target compounds to the resin is not very high unless a high salt concentration is employed in the target compound solution. For example, in Kasche, et al. [7], protein binding to the resin on a preparative level was effected using a 1M NaCl solution. Chromatographic techniques involving the addition of salt to an aqueous solution containing the target compound require the use of large quantities of reagents to effect recovery on an industrial scale and may necessitate substantial processing. Accordingly, chromatographic resins requiring the use of high salt concentrations are not the most efficient and cost effective methods for recovering and/or purifying industrial quantities of such compounds.

This invention is directed, in part, to the discovery that the use of a high ligand density on a mixed mode chromatographic resin coupled with the use of a specific ionizable ligand comprising an ionizable functionality and a spacer arm which covalently links the ligand to the solid support matrix of the resin can provide for sufficient hydrophobic character in the resin such that the target compound binds to the resin at high and low ionic strength. This invention is further directed, in part, to the discovery that target compound desorption from the resin can be achieved by hydrophilic or electrostatic (ionic) interactions by merely altering the pH of the desorbing solution such as to increase the amount of charge on the resin via the ionizable functionality. This latter feature provides a significant advantage over high density HIC resins by providing a facile means to provide product recovery whereas binding to such HIC resins can often be irreversible.

In this invention, the ionizable ligand is rationally selected relative to the target compound thereby permitting the efficient large scale recovery and/or purification of a target compound from an aqueous medium including a fermentation broth. The resins employed herein are specifically characterized as comprising a solid support matrix and selected ionizable ligands or mixtures of selected ionizable ligands covalently attached to the solid support matrix at a density greater than the smaller of either at least 150 µmol per milliliter of resin or 1 mmol per gram dry weight of resin. The ionizable ligands comprise a spacer arm and at least one ionizable functionality which functionality is bound to the matrix through the spacer arm. The ionizable ligand employed on the resin is selected relative to the solid support matrix and the target compound such that the hydrophobic character of the resin is sufficient to bind at least 50% of the target compound in an aqueous medium at high and low ionic strength at a first pH and is further selected relative to the solid support matrix and the target compound such that the hydrophilic and/or electrostatic (ionic) character of the resin at a second pH is sufficient to desorb the bound compound at said second pH. Additionally, the ionizable functionality is partially electrostatically charged at the pH of binding of the compound to the resin and is either further charged or charged at a different polarity the pH of desorption of the compound from the resin. Such partially charged resins may provide a secondary basis for enhancing or weakening the binding of the target compound to the resin.

In a preferred embodiment, the electrostatic charge on the resin at the pH where the target compound is desorbed from the resin is of the same polarity as the net electrostatic charge on the target compound at the desorption pH. In this embodiment, desorption is achieved by charge-charge repulsions which offset the hydrophobic binding character of the resin. In another embodiment, the electrostatic charge on the resin at the pH where the target compound is desorbed from the resin is of opposite polarity from that of the target compound. In either embodiment, desorption can be facilitated by use of desorbing solution (e.g., eluants) of high ionic strength or by use of a polarity reducing agent, such as ethylene or propylene glycol.

The resins of this invention are contrasted with mixed-mode resins heretofore described by the character that the resin comprises a ligand density greater than the smaller of either at least 150 µmols per milliliter of resin or 1 mmol per gram dry weight of resin and further by the character that the ligand contain a spacer arm which covalently links an ionizable functionality to the matrix. Specifically, in the literature, ionizable groups have been deliberately introduced [2,3] to weaken strong binding to long alkyl chain (hydrophobic) Sepharose resins and allow more favorable desorption conditions. The ligand density on these matrices has been calculated to be about 15–21 µmol per milliliter.

A polystyrene carboxyl resin (Amberlite) has also been used for protein binding by hydrophobic interactions [8,9] and desorption by ionic interaction. However, while a high density of carboxyl groups is employed, there is no spacer arm linking the carboxyl groups to the solid support matrix.

Also disclosed are resins which are positively charged with isourea groups [4,5] having a density believed to be about 20 µmol per milliliter or less. These resins are weakly hydrophobic and typically require electrostatic and hydrophobic interactions for binding of the target compound to the resin.

Binding of target compounds at high and low ionic strength to the resins of this invention which resins contain ionizable functionality is in contrast to the resins of the prior art having ionizable functionality which typically require adjustments in the ionic strength of the solution either prior to binding of the target compound or to effect desorption of the target compound from the resin. Such adjustments are not consistent with an efficient industrial scale process to effect target compound recovery and/or purification.

SUMMARY OF THE INVENTION

This invention relates, in part, to specifically designed mixed mode chromatographic resins which are useful in recovering a target compound, such as a protein or a peptide, from an aqueous medium and methods for use of such resins. The resins described herein comprise a solid support matrix and ionizable ligands which ligands comprises an ionizable functionality and a spacer arm covalently attaching the ligand to the solid support matrix. The ionizable functionality is partially electrostatically charged at the pH of binding of the compound to the resin and is either further charged or charged at a different polarity at the pH of desorption of the compound from the resin.

These resins are particularly characterized as having an ionizable ligand density on the resin greater than the smaller of at least 150 µmols per milliliter of resin or 1 mmol per gram dry weight of resin wherein the ionizable ligand is selected relative to the solid support matrix and the target compound such that the hydrophobic character of the resin is sufficient to bind at least 50% of the target compound in an aqueous medium at high and low ionic strength at a first pH and is further selected such that the hydrophilic and/or electrostatic character of the resin at a second pH is sufficient to desorb the bound compound at said second pH.

Accordingly, in one of its composition aspects, this invention is directed to a resin for binding a target compound which comprises a solid support matrix, selected ionizable ligands or mixtures of selected ionizable ligands covalently attached to the solid support matrix wherein the ionizable ligand comprises a spacer arm and at least one ionizable functionality which functionality is bound to the matrix through the spacer arm, wherein the density of the ionizable ligands on the solid support matrix is greater than the smaller of either about 150 µmol per milliliter of resin or 1 mmol per gram dry weight of resin, the ionizable ligand being selected relative to the solid support matrix and the target compound such that the hydrophobic character of the resin is sufficient to bind at least 50% of the target compound in an aqueous medium at high and low ionic strength at a first pH and is further selected relative to the solid support matrix such that the hydrophilic and/or electrostatic character of the resin at a second pit is sufficient to desorb the bound compound at said second pH, and the ionizable functionality being either further electrostatically charged or charged at a different polarity at the pH the target compound is desorbed from the resin as compared to the charge at the pit of target compound binding to the resin.

In a preferred embodiment, such resins optionally comprise selected non-ionizable ligands covalently attached to the solid support matrix wherein the percentage of non-ionizable ligands based on the total of ionizable and non-ionizable ligands ranges from about 0 to 80%. In this embodiment, the mount of non-ionizable ligand is selected relative to the mount of ionizable ligand and the solid support matrix such that the hydrophobic character of the resin is sufficient to bind at least 50% of the target compound in an aqueous medium at high and low ionic strength at a first pH and is further selected relative to the solid support matrix such that the hydrophilic and/or electrostatic character of the resin at a second pH is sufficient to desorb the bound compound at said second pH.

In one of its method aspects, this invention is directed to a method for separating a target compound from an aqueous medium comprising the target compound which method comprises contacting the medium with a resin as described above under conditions suitable for binding at least 50% of the target compound binds to the resin, including adjusting the pH of the medium.

In still another of its method aspects, this invention is directed to a method for binding and recovering a target compound from an aqueous medium comprising the target compound which method comprises:

a) contacting the medium with a resin as described above under conditions suitable for binding at least 50% of the target compound to the resin;

b) separating the resin containing the bound target compound from the other components of the medium to produce a resin-compound complex; and c) desorbing the bound target compound from the complex by contacting the complex with an chant having a pH sufficiently different from the pH of the medium recited in a) above such that the target compound desorbs from the resin.

In another of its composition aspects, this invention is directed to novel resins having ionizable functional groups pendant to a solid support matrix which resins comprise:

a solid support matrix; and an ionizable ligand which comprises an ionizable functionality and a spacer arm which covalently attaches the ionizable functionality to the solid support matrix wherein said ionizable functionality is derived from a compound selected from the group consisting of 4-(aminomethyl) pyridine, 3-(aminomethyl)pyridine, 2-(aminomethyl) pyridine, 1-(3-aminopropyl)-imidazole, 2-(aminomethyl)- benzimidazole, 4-(3-aminopropyl)morpholine, halotryamines having from 1 to 2 halo groups selected from the group consisting of fluoro, chloro, bromo and iodo, 4-aminobutyric acid, (1S, 2S)-(+)-2-amino-1-phenyl-1,3-propanediol, (−)-phenylpropanolamine, phenylethylamine, phenylalaninol, 4-(2-aminoethyl)benzenesulfonamide, DL-β-hydroxyphenylethylamine, thiosalicylic acid, 2-mercapto-1-methylimidazole, 2-mercaptobenzimidazole, 4-mercaptoethylpyridine, 2-mercaptoethylpyridine, 4-mercaptobutyric acid, 5-mercaptovaleric acid, 6-mercaptohexanoic acid, 4-hydroxythiophenol, 4-hydroxybenzoic acid, 4-hydroxyphenylacetic acid, 3-chlorohydroxyphenylacetic acid, 3,5-dichlorosalicylic acid, 4-hydroxy-3-nitrobenzoic acid, 3-nitrotyrosine, and halotyrosines having from 1 to 2 halo groups selected from the group consisting of fluoro, chloro, bromo and iodoparahydroxybenzoic acid hydrazide.

In still another of its composition aspects, this invention is directed to novel resins having ionizable functional groups pendant to a solid support matrix which resins comprise:

a solid support matrix; and ionizable ligands pendant to said support at a density greater than the smaller of at least about 150 μmol per milliliter of resin or 1 mmol per gram dry weight of resin which comprise an ionizable functionality and a spacer arm which covalently attaches the ionizable functionality to the solid support matrix wherein said ionizable functionality is derived from a compound selected from the group consisting of aminocaproic acid, 2-mercaptopyridine, 4-mercaptopyridine, aminoethylbenzenesulfonamide, tyramine, tyrosine, and histidine.

BRIEF DESCRIPTION OF THE DRAWINGS

FIG. 1 illustrates ligand attachment to carbonyl diimidazole (CDI) activated matrices.

FIG. 2 illustrates carbodiimide coupling of ligands to matrix carboxyl groups.

FIG. 8 illustrates a typical elution profile of the recovery of subtilisin from a crude fermentation broth containing subtilisin using a radial flow column.

DETAILED DESCRIPTION OF THE INVENTION

Figure 3:
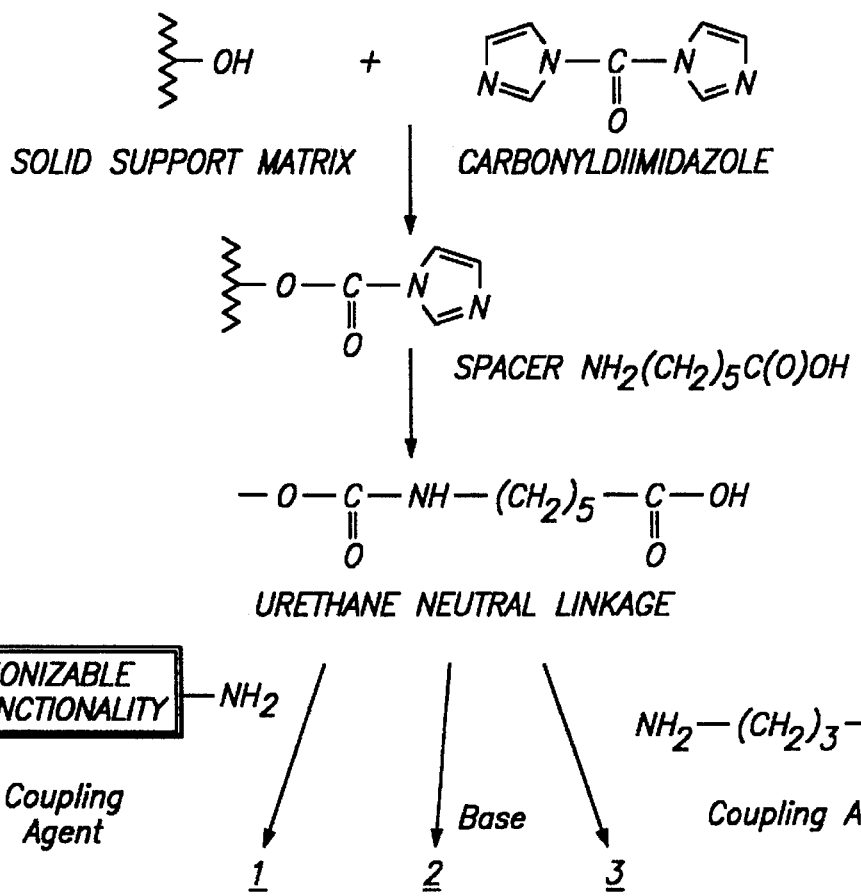
FIG. 3 illustrates CDI-caproic acid supports.

This invention is directed, in part, to rational methods for recovering a target compound from an aqueous medium using resins. The methods of this invention are directed, in part, to the selection of a resin for use in the recovery of the target compound from an aqueous media wherein the hydrophobic character of the resin is sufficient to bind at least 50% of the target compound in an aqueous medium at high and low ionic strength at a first pH and further wherein the hydrophilic and/or electrostatic character of the resin at a second pH is sufficient to desorb the bound compound at said second pH. The ionizable ligands of the resins of this invention are selected relative to the solid support matrix as well as the properties of the target compound such as its electrostatic charge, pI, stability, etc. so that the pHs where the resin has a hydrophobic character and a hydrophilic and/or electrostatic character correspond to a pH range where the target compound is sufficiently stable, etc. One skilled in the art can readily ascertain such parameters based on the teachings herein.

In a preferred aspect of this embodiment, the selection process is extended to include the selection of the solid support matrix employed in conjunction with the ionizable ligand and the density of such ligands on the matrix wherein the selection is made relative to the degree of hydrophobicity required for the overall resin at the pHs of binding and desorption of the target compound from the resin. In this regard, the solid support matrix can be either free of ionizable functionality or can contain ionizable functionality.

Additionally, both the ionizable functionality as well as the spacer arm of the ionizable ligand are selected to provide further control over the hydrophobicity at the pHs of target compound binding and desorption.

In a further preferred aspect of this embodiment, the selection process is also extended to include the selection of one or more non-ionizable ligands relative to the degree of hydrophobicity required for the overall resin at the pHs of binding and desorption. For example, the hydrophobicity of a resin can be adjusted to increase binding of the target compound, if binding needs to be increased, by employing non-ionizable ligands pendant to the solid support matrix wherein the hydrophobicity of the ligand is controlled. For example, very hydrophobic non-ionizable ligands such as one incorporating aromatic groups can be employed to increase the overall hydrophobicity of the resin whereas a more hydrophilic non-ionizable ligand such as one containing several non-ionizable alcohol groups (e.g., alkanols) can be employed to enhance the overall hydrophilicity of the resin relative to the requisite hydrophobicity/hydrophilicity required to effect binding of the target compound to and desorption of the target compound from the resin.

By making the appropriate selection for each of the components of the resin, the hydrophobic character of the resin at the pH of target compound binding thereto can be rationally selected to enhance the binding efficiency and/or increase binding specificity of the target compound to the resin. Likewise, the hydrophilic and/or electrostatic (ionic) character of the resin at the pH of target compound desorption from the resin can be rationally selected so as to ensure proper desorption of the target compound from the resin.

Prior to describing this invention in more detail, the following terms will first be defined.

Definitions

The term "target compound" refers to the particular compound or compounds one wishes to isolate from an aqueous solution. The target compound can be a protein, a peptide, a nucleotide, an oligonucleotide, a saccharide, an oligosaccharide, a carbohydrate, asteroid, a cyclic aromatic compound, a diol, an indole derivative, a pharmaceutical chemical compound or intermediate thereof, a primary or secondary cellular metabolite, and the like. The particular target compound is not critical. However, in a preferred embodiment, the target compound is selected from the group consisting of a protein or a peptide, a primary or secondary cellular metabolite, and a pharmaceutical chemical intermediate.

The term "solid support matrix" or "solid matfix" refers to the solid backbone material of the resin which material contains reactive functionality permitting the covalent attachment of ligand thereto. The backbone material can be inorganic (e.g., silica) or organic. When the backbone material is organic, it is preferably a solid polymer and suitable organic polymers are well known in the art. Solid support matrices suitable for use in the resins described herein include, by way of example, cellulose, regenerated cellulose, agarose, silica, coated silica, dextran, polymers (such as polyacrylates, polystyrene, polyacrylamide, polymethacrylamide including commercially available polymers such as Fractogel, Enzacryl, and Azlactone), copolymers (such as copolymers of styrene and divinyl-benzene), mixtures thereof and the like. Also, co-, ter- and higher polymers can be used provided that at least one of the monomers contains or can be derivatized to contain a reactive functionality in the resulting polymer. In an additional embodiment, the solid support matrix can contain ionizable functionality incorporated into the backbone thereof. For example, suitable matrices include, by way of example, the well known polyethylene amines as well as any other matrices employing secondary or tertiary amines. Preferably, however, the solid support matrix does not contain any ionizable functionality.

Reactive functionalities of the solid support matrix permitting covalent attachment of the ligand are well known in the art. Such groups include hydroxyl (e.g., Si-OH), carboxyl, thiol, amino, and the like. Conventional chemistry permits use of these functional groups to covalently attach ligands thereto. Additionally, conventional chemistry permits the inclusion of such groups on the solid support matrix. For example, carboxyl groups can be incorporated directly by employing acrylic acid or an ester thereof in the polymerization process. Upon polymerization, carboxyl groups are present if acrylic acid is employed or the polymer can be derivatized to contain carboxyl groups if an acrylate ester is employed.

The term "ionizable ligand" refers to a group comprising an ionizable functionality and a spacer arm for covalently attaching the ligand to the solid support matrix wherein the ionizable functionality contains one or more groups capable of being electrostatically charged at one pH and electrostatically uncharged at another pH. Suitable ionizable functional groups include by way of example, amine groups, phenolic groups, carboxyl groups, histidyl groups, pyridyl groups, anilino groups, morpholinyl groups, imidazolyl groups, and the like. Substituents can be included on ionizable functionality or the spacer arm for the purpose of modifying the pH at which the ionizable ligand will begin to titrate. For example, inclusion of one or more nitro groups, halo groups, alkyl groups, etc. on a phenol group will change the pH at which this group will be electrostatically charged. Such modification of ligands is well within the skill of the art.

The spacer arm refers to any group or substituent which covalently attaches the ionizable functionality to the solid support matrix. Such spacer arms are well known in the art and include, by way of example only, alkylene groups, aromatic groups, alkylaromatic groups, amido groups, amino groups, urea groups, carbamate groups, —$R_1$—Y—$R_2$— groups where $R_1$ and $R_2$ are an alkylene groups (e.g., $C_1$–$C_6$) and Y is oxygen or sulfur, and the like.

The term "selected ionizable ligand" refers to the ligand or mixture of ligands selected for covalent attachment to the solid support matrix. Selection of the ionizable ligand is made relative to the pH where the ligand will have a hydrophobic character and where the ligand which will have a hydrophilic and/or electrostatic character as well as the stability of the resin at these pHs. In turn, the pHs selected for binding and desorption will depend on the physical and chemical properties of the target compound and stability of the target compound at these pHs.

The term "partially electrostatically charged at the pH where the target compound is bound to the resin" means that greater than 5% to less 100% of the ionizable functionalities on the resin are charged at the pH of target compound binding. Preferably, from greater than 5% to about 40% of the ionizable functionalities on the resin are charged at this pH.

The term "a non-ionizable ligand" refers to a group covalently attached to the solid support matrix either directly or indirectly through a spacer arm which group does not contain any readily ionizable functionality. Suitable non-ionizable ligands include, by way of example, alkyl groups, aromatic groups (e.g., phenyl, naphthyl) and alkylaromatic groups (e.g. benzyl groups).

The term "high ionic strength" means an ionic strength greater than or equal to that required to provide a specific conductance (conductivity) of about 24.3 millimho (milliSiemens). For example, such conductance can be reached by using 250 millimolar (mM) sodium chloride. The term "low ionic strength" means an ionic strength less than that required to provide a specific conductance of less than 24.3 millimho. Procedures for determining the specific conductance of a solution are well known to those skilled in the art.

Methodology

The use of chromatographic resins in the purification of target compounds is well known in the art. These resins normally comprise a granular or beaded solid support matrix to which ligands are bound either directly thereto or through a spacer arm. An aqueous solution containing a target compound is contacted with the resin. Interactions between the resin and the target compound based on, for example, chemical charge, relative hydrophobicity, or specific affinity allow the target compound in the solution to bind to the resin. By specifically altering the conditions of the desorption buffer to counter the interactions between resin and the target compound, the target compound can be selectively recovered.

The methods described herein represent an improvement over the chromatographic recovery methods of the prior art insofar as these methods provide for a highly efficient means to recover industrial quantities of the target compound from an aqueous medium such as a fermentation broth. In one particularly preferred embodiment, the methods described herein are particularly useful in purifying proteins from fermentation broth (e.g., chymosin and subtilisin) because purification may often be accomplished directly from a crude broth preparation and further because components of the crude clarified broth other than the target protein may not bind to these matrices.

The methods described herein are particularly useful where very high target compound purity is not required, e.g., industrial enzymes, because this level of purity can be attained with one step purification. Optionally, broths can be loaded after pH adjustment, if required, without dilution, concentration, desalting, salt addition or particulate removal. Similarly, desorption of the target compound from the resin can be achieved merely by pH adjustment without the necessity of salting or desalting. It is contemplated that the resins described herein may be less susceptible to fouling and easier to regenerate than resins which cannot be ionized.

The resins described herein provide a combination of several important features. They may allow direct recovery of a target compound from a crude aqueous solution, and may allow significant purification at the start of downstream processing. Desorption into low ionic strength buffers may be well suited for a subsequent step in chromatographic processing, i.e., before ion exchange or affinity chromatography. They allow rapid, inexpensive elution under non-harsh conditions. Minimal step or gradient technology is required, little or no extra salt is required, and little or no solvent may be required.

Due to the general nature of the binding in the methods of this invention, these methods may exhibit less specificity than other chromatographic procedures. For example, in the case of fermentation broth processing, the broth may have different major protein contaminant(s) with different hydrophobicities [19]. Therefore, a significant level of non-target protein binding may occur.

Purification or fractionation using the methods described herein requires that target compound hydrophobicity and/or isoelectric point (pI—if appropriate) differ from that of most contaminants. Target compounds with similar hydrophobicity and isoelectric point as non-target compound contaminants may co-elute with the contaminants in the absence of gradient desorption. This can be countered by sample pretreatment or ligand, spacer and matrix variations, as described in detail herein. Additionally, since compound binding is accomplished at both high or low ionic strength in the methods described herein, change of the ionic strength of the solution contacting the resin may remove some impurities while retaining the target proteins bound to the resin. Also, change of pH at low ionic strength may be useful in selectively desorbing one target compound over another. On the other hand quantitative compound binding and recovery is a preference in some processes, e.g., whey protein recovery. The methods described herein may also be useful for non-covalent enzyme immobilization [14–18], because binding is strong and enzyme recovery is simple.

The methods described herein below employ specific resins useful for the binding of target compounds. Binding to these resins is accomplished at a pH where the resin has a hydrophobic character and, accordingly, binding is achieved principally by hydrophobic interactions notwithstanding the fact that the ionizable ligands on the resin at this pH are partially charged. The degree of hydrophobic interaction between the resin and the target compound at the pH of binding is rationally selected so that the strength of target compound binding to the resin is controlled. Such selection is achieved by use of suitable matrices and ligands, including the spacer arms employed therewith, where the combination of these materials provides for controlled hydrophobicity of the resin.

One means to further control hydrophobicity is to include a population of non-ionizable ligands on the solid support matrix being either highly hydrophobic (e.g., containing phenyl or benzyl groups) or more hydrophilic (e.g., containing amide, urethane or non-ionizable hydroxyl groups). Such factors are well within the skill of the art based on the teachings herein. Preferably, when non-ionizable ligands are employed, the population of non-ionizable ligands on the solid support matrix will range from 0 to 80 percent based on the total number of ionizable plus non-ionizable ligands.

Additionally, when a ligand is attached to the solid support matrix through a thioether bond, the hydrophobicity of the resin may be controlled by oxidizing some or all of the sulfur atoms in the resin to sulfoxide and/or sulfone groups. By increasing the population of sulfoxide and/or sulfone groups present in the resin, the hydrophobicity of the resin is reduced. Suitable procedures for oxidizing thioether groups to sulfoxide or sulfone groups are well known in the art.

The methods described herein are useful for recovering a broad range of target compounds including proteins and peptides including recombinant products. The methods may also be used to perform compound separations on extracts from natural sources, such as plant and animal sources.

The resins described herein employ ionizable and optionally non-ionizable ligands attached to solid support matrices. Any method of covalent attachment of the ligands maybe used, provided that the attachment does not result in introduction of ionizable groups other than the desired ionizable group(s). Examples of methods for attachment of such ligands to the solid support matrices include covalent thioether, ether, amide, amine and urethane bonds. Other thioether methods, disulfide attachment, and urea methods may also be used. Additionally, hydrazide ligands may be attached to epoxide or aldehyde functional groups. In the case of attachment through the aldehyde subsequent reduction of the imine (e.g., with sodium cyanoborohydride) is preferred.

Representative ligand attachment chemistries are shown in Table 1. Other ligand attachment chemistries are illustrated elsewhere herein and/or are known in the art.

TABLE 1

Ligand Attachment Chemistries

| Matrix Functional Group | Activation Chemistry | Ligand Reactive Group | Linkage |
|---|---|---|---|
| Hydroxyl | carbonyl diimidazole | amine | urethane |
| | epoxide | amine | amine |
| | | thiol | thioether |
| | | hydroxyl | ether |
| | CNBr | amine | various |
| | tosyl chloride | amine | amine |
| | | thiol | thioether |
| | divinylsulfone | amine | amine |
| | | thiol | thioether |
| | | hydroxyl | ether |
| Carboxyl | carbodiimide | amine | amide |
| Amine | carbodiimide | carboxyl | amide |
| Amide | hydrazine/HNO$_2$ | amine | amide |

Figure 4:
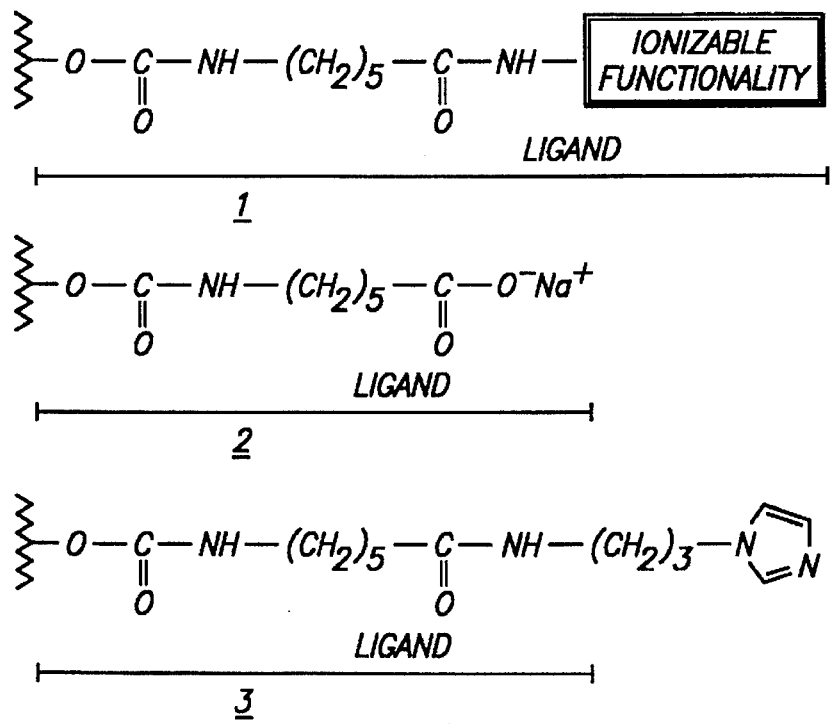
FIG. 4 illustrates possible products from condensation (reaction) of an amine with a CDI-caproic acid matrix.

Each of these chemistries is well known in the art and coupling results in the linkage described above. For example, the ligands may be attached to the solid support matrix such as activated cellulose matrix through a neutral urethane bond by use of carbonyl diimidazole (CDI) reagent as illustrated in FIGS. 1 and 3. Alternatively, the ligands may be attached through an amide bond to a cellulose matrix derivatized with an aminocaproic acid spacer arm as illustrated in FIG. 4, embodiments 1 and 3. Where necessary, 100% substitution of spacer arm carboxyl groups can be achieved. Such substitution can be confirmed using procedures well known in the art, such as small ion titration.

Ligand attachment via carbonyl diimidazole (CDI) activated matrices is illustrated in FIG. 1. Carbodiimide coupling of the ligand to matrix carboxyl groups is illustrated in FIG. 2. CDI-caproic acid supports are illustrated in FIG. 3. Possible derivations of the CDI-caproic matrices are illustrated in FIG. 4.

Figure 5:
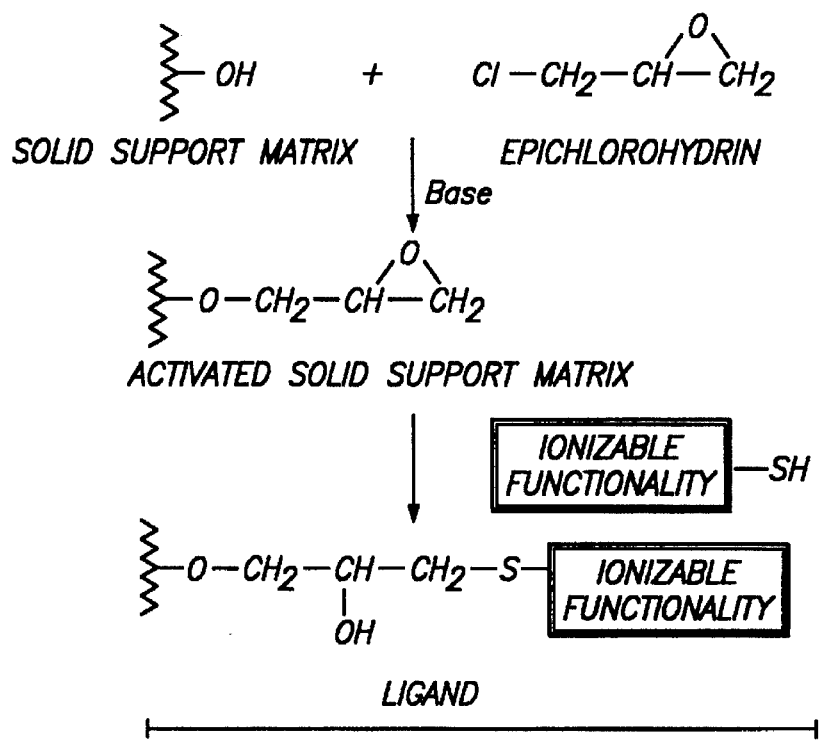
FIG. 5 illustrates reaction of an thiol with epoxy activated matrices.
Figure 6:
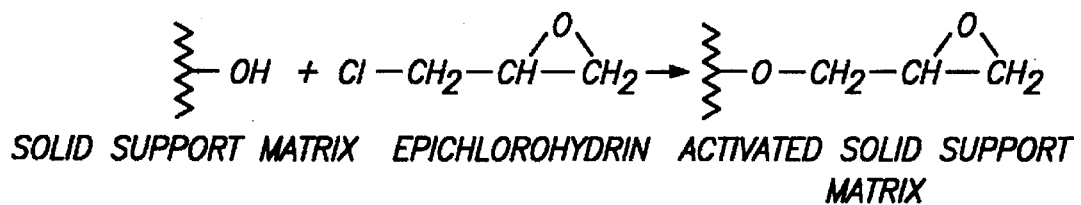
FIG. 6 illustrates reaction of an amine with an epoxide activated matrix wherein the ionizable amine functionality is retained.
Figure 6:
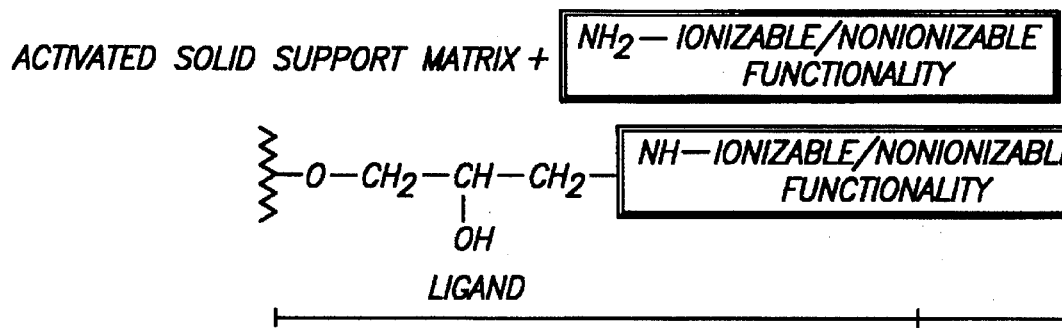
Figure 7:
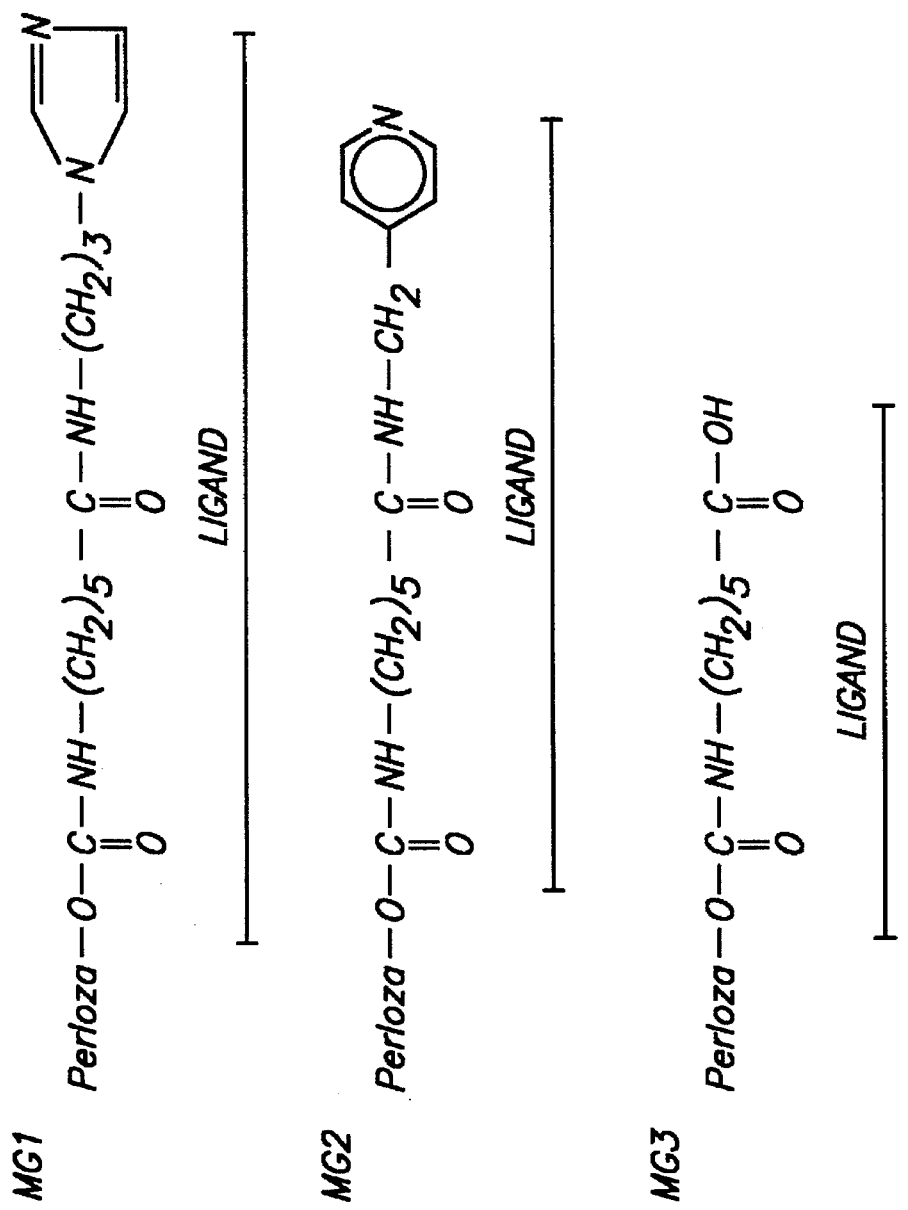
FIG. 7 illustrates the structure of some resins useful in the present invention.

Alternative to CDI activated matrices for ligand attachment are resins containing epoxide groups whose preparation and ligand attachment thereto are exemplified in FIGS. 5 and 6. Specifically, FIG. 5 illustrates attachment of thiol containing ligands to an epoxide activated solid support matrix. In this resin, the ligand is attached through a stable, neutral thioether bond [10]. Ligands which can be used with this chemistry include, by way of example, mercaptobenzimidazole, 4-mercaptopyridine, 2-mercaptopyridine, methimazole and 4-hydroxythiophenol. FIG. 6 illustrates the reaction of an amine with an epoxide activated solid support matrix. The chemistry used in both cases is typically aqueous and therefore less expensive than the CDI method. However, this chemistry can introduce cross-linking into the matrix which may reduce loading capacity. As illustrated in FIG. 6, the ionizable amine functionality is retained in the resulting ligand and, accordingly, the group attached to the amine in this figure can either contain further ionizable functionality (e.g., pyridine, —CH$_2$-pyridine) or can be non-ionizable (e.g., alkyl).

Other preferred activation agents for matrix modification with thiol ligands have one highly reactive group and one group which can be derivatized to a reactive group. The highly reactive group reacts with a matrix hydroxyl group at alkaline pH to form a stable bond, while the second group does not react under these conditions. This prevents cross-linking. After the first activation step, the second group is derivatized to a reactive group which can then be reacted directly. Allyl halides (e.g., allyl bromide) and allyl glycidyl ether are preferred reagents. Other reagents include, by way of example, 2 and 4-vinylpyridine, 2- and 4-mercaptoethylpyridines, and aminopyridines. For example, solid support matrices activated with allyl glycidyl ether can permit substitution levels greater than those activated with epichlorohydrin. Upon covalent attachment of these ligands to the resin, the allyl group can be modified so as to incorporate an ionizable functionality (e.g., reaction with bromine water to form the bromo derivative followed by reaction with the his sodium salt of 4-hydroxybenzoic acid).

It is understood that the ionizable functionality can be incorporated into the solid support matrix. For example, a polyamine or a polymer comprising amine functionality can be used wherein the amine functional groups are ionizable at low pHs. In such an embodiment, the polymer can be prepared to include other functional groups and ligand attachment can be made either through the amine groups or such other functional groups. In the former embodiment, ligand attachment chemistries are employed to retain at least a portion of the ionizable functionality on the backbone of the matrix.

Ionizable ligands useful on the resins described herein include those derived by covalently linking 3-(aminomethyl)pyridine (3AMP), 4-(aminomethyl)pyridine (4AMP), 1-(3-aminopropyl)imidazole (API), 2-(aminomethyl)benzimidazole (AMB), 4-(3-aminopropyl)morpholine (APM), histamine, and the like to the solid support matrix employing the chemistry described above in Table 1 and in the Examples herein below. Other suitable compounds for forming the resins of this invention include 4-(aminomethyl)pyridine, 2-(aminomethyl)pyridine, halotryamines having from 1 to 2 halo groups selected from the group consisting of fluoro, chloro, bromo and iodo, 4-aminobutyric acid, (1S, 2S)-(+)-2-amino-1-phenyl-1,3-propanediol, (−)-phenylpropanolamine, phenylethylamine, phenylalaninol, 4-(2-aminoethyl)benzenesulfonamide, DL-β-hydroxy-phenylethylamine, thiosalicylic acid, 2-mercapto-1-methylimidazole, 2-mercaptobenzimidazole, 4-mercaptoethylpyridine, 2-mercaptoethylpyridine, 4-mercaptobutyric acid, 5-mercaptovaleric acid, 6-mercaptohexanoic acid, 4-hydroxythiophenol, 4-hydroxybenzoic acid, 4-hydroxyphenylacetic acid, 3-chlorohydroxyphenylacetic acid, 3,5-dichlorosalicylic acid, 4-hydroxy-3-nitrobenzoic acid, 3-nitrotyrosine, tyrosine, halotrosines having from 1 to 2 halo groups selected from the group consisting of fluoro, chloro, bromo and iodo histidine, aniline, and para-hydroxybenzoic acid hydrazide.

When a hydrophobic amine compound is used to generate the ionizable or non-ionizable ligand, it is preferably selected from the group consisting of 2-phenylethylamine, L-phenylalaninol, (1R, 2S)-(−)-phenylpropanolamine, tryptamine, 4-(2-aminoethyl)benzenesulfonamide, (1S, 2S)-(+)-2-aminophenylpropanediol and 1-hexylamine. When ionizable ligands are to be generated, the amine group is retained in these molecules, for example, by reaction with an epoxide and the amine forms part of the linking arm. When non-ionizable ligands are to be generated, the amine group is reactively eliminated from the molecule by, for example, reaction with a carboxylic acid so as to generate an amide.

Other useful ligands include those containing unsubstituted phenol and substituted phenols with pKa's in the 6–9 range. Suitable substituents for the phenyl group include nitro, halo (e.g., chloro, bromo), alkyl of from 1–10 carbon atoms, alkoxy of from 1–10 carbon atoms, carboxyl esters where the ester group is from 1 to 10 carbon atoms, cyano, carbonyl alkyl (—C(O)R) groups of from 1–10 carbon atoms, and mixtures thereof. Typically, substituted phenyl groups have from 1 to 4 such substituents and preferably from 1 to 2. The above substituents can also be attached to other substitutable ligands including ligands containing pyridyl groups, histidyl groups, indolyl groups, imidazolyl groups, morpholinyl groups, benzimidazolyl groups and the like.

The list of ionizable ligands set forth herein is not intended to be exhaustive nor is the chemistry employed to covalently attach these ligands to the solid support matrix. Suffice it to note that the attachment of suitable ligands to the solid support matrix employs chemistry well known in the art.

The ionizable ligand is preferably present on the resin at a sufficient concentration to permit target protein binding at both high and low ionic strength. Preferably, the ionizable functionality will be present on the resin at a concentration of greater than the smaller of at least about 1 mmol per gram dry weight of resin or at least about 150 µmol/ml of resin. In one particularly preferred embodiment, non-ionizable ligands are employed in conjunction with ionizable functionality so as to provide for further control over the degree of hydrophobicity/hydrophilicity at the pH of target compound binding to and desorption from the resin. In this embodiment, the percentage of non-ionizable ligands relative to the total number of ligands ranges from about 0 to about 80 percent, preferably from 0 to 40 percent.

In the methods of this invention, a solution or aqueous medium comprising the target compound to be recovered is contacted with the resin at a pH where the hydrophobic character of the resin is sufficient to bind at least 50% of the target compound at high and low ionic strength. At this pH, binding is primarily by hydrophobic interaction and the degree of hydrophobicity of the resin can be adjusted by modification of the spacer arms and/or ionizable functionality comprising the ligand, by employing a more or less hydrophobic solid support matrix, by use of non-ionizable ligands, by increasing the density of ligands on the solid support matrix and combinations thereof. In view of the teachings herein, one skilled in the art can rationally adjust these parameters based on the properties of the target compound coupled with the enhancements desired.

The medium comprising the target compound, e.g., a protein such as chymosin, to be recovered may be derived from any known sources, including microbial or animal sources. For example, chymosin solutions can include fermentation broth from Aspergillus, *E. coli*, yeast, as well as aqueous extracts obtained from bovine abomasa.

The aqueous medium may include a buffer and/or a salt to enhance binding efficiencies to the resin. However, as noted above, binding of the target compound can be achieved at high and low ionic strength and, accordingly, the addition of salt to the aqueous medium is merely to provide further binding. Suitable salts are those conventionally employed in chromatography and include, by way of example, the lithium, sodium, potassium, ammonium, calcium and magnesium salts of chloride, sulfate, phosphate and acetate. Preferably, sodium chloride is employed because it is effective, inexpensive and safe.

As noted above, the resins described herein will bind target compound from aqueous media at both high and low ionic strengths. Specifically, these resins will bind about 50 percent or more of the target compound in the aqueous medium at low and high ionic strengths. It being understood, of course, that the volume of resin employed has sufficient capacity to bind all of the target protein in the medium.

The aqueous medium is contacted with the resin for a time sufficient to allow the target compound to bind to the resin. This contact may be made, for example, where the resin is packed in a column, employed in a fluidized bed, or suspended in a stirred batch system where the resin is mixed with the aqueous medium. Under such conditions, the target compound binds to the resin thereby forming a resin-compound complex. After contacting the aqueous medium with the resin, the resin is then washed with a buffer of pH equal to that of the aqueous medium to separate the aqueous medium from the resin and the compounds bound thereon. This buffer may additionally comprise at least up to 2M salt as listed above.

The target compound is then desorbed from the resin merely by contacting the resin with an aqueous medium having a pH which alters the character of the resin from a hydrophobic character to a hydrophilic and/or electrostatic character. This is achieved by selecting a pH where the ionizable functionalities on the ligand become more charged or carry a charge of different polarity from that of the ligands at the pH of target compound binding. It being understood that desorption from the resin may also be facilitated by changes in the binding properties of the target compound at the pH of desorption.

In a preferred embodiment of the present invention, the charge on the resin at the pH of desorption is of the same polarity as the net electrostatic charge on the target compound at the pH of desorption and the resulting charge-charge repulsions between the resin and the target compound being sufficient to overcome any hydrophobic interactions with the resin thereby facilitating desorption from the resin. This can be achieved by rationally selecting the relative hydrophobicity of the resin as described above and/or by incorporation of sufficient ionizable ligands to provide for an effectively large electrostatic charge on the resin at the pH of desorption.

In another embodiment of the present invention, the induced charge on the resin is of the opposite polarity from the net electrostatic charge on the target compound at the pH of desorption. In this embodiment, desorption of the target compound from the resin can be facilitated by, for example, use of an eluant of high ionic strength. In either embodiment, the use of a polarity reducing agent, such as ethylene or propylene glycol, can facilitate desorption of the target compound from the resin.

Ligand choice is based on target compound pH constraints. For example, in certain circumstances, it may be desirable to use a resin having ligands with ionizable functionality which becomes positively charged at pHs where the target compound is stable so that extreme pHs can be avoided for compound binding or desorption. Likewise, resins having ligands with ionizable functionality which becomes negatively charged at pHs where the compound is stable may be preferred. Compounds having ionizable functionality useful as ligands herein include, by way of example, caproic acid, including 6-aminocaproic acid, (titrates from pH≈3.3). Phenolic compounds, e.g., tyramine, are also useful in this regard since the hydroxyl group of phenol titrates from about pH 6 and above. Nitrated or chlorinated phenol or tyramine ligands are especially useful since they have a pKa value near neutral pH. Still other compounds having ionizable functionality useful as ligands herein include, by way of example only, 4-(aminomethyl) pyridine, 3-(aminomethyl)pyridine, 2-(aminomethyl)

pyridine, 1-(3-aminopropyl)-imidazole, 2-(aminomethyl)-benzimidazole, 4-(3-amino-propyl)morpholine, halotryamines having from 1 to 2 halo groups selected from the group consisting of fluoro, chloro, bromo and iodo, 4-amino-butyric acid, (1S, 2S)-( +)-2-amino-1-phenyl-1,3-propanediol, (–)-phenylpropanolamine, phenylethylamine, phenylalaninol, 4-(2-aminoethyl)benzenesulfonamide, DL-β-hydroxyphenylethylamine, thiosalicylic acid, 2-mercapto-1-methylimidazole, 2-mercaptobenzimidazole, 4-mercaptoethylpyridine, 2-mercaptoethylpyridine, 4-mercaptobutyric acid, 5-mercaptovaleric acid, 6-mercaptohexanoic acid, 4-hydroxythiophenol, 4-hydroxybenzoic acid, 4-hydroxyphenylacetic acid, 3-chlorohydroxyphenylacetic acid, 3,5-dichlorosalicylic acid, 4-hydroxy-3-nitrobenzoic acid, 3-nitrotyrosine, tyrosine, halotyrosines, histidine, and para-hydroxybenzoic acid hydrazide.

In another embodiment where the target compound (e.g., a protein) is stable only at physiological pHs (i.e., pHs of from 5 to 9) the ionizable ligands attached to the solid support matrix should provide resins which titrate fully or partially in a pH range of from about 5 to 9 and more preferably from about 5.5 to about 8.5. Such a range permits binding and desorption of a target protein at a pH range which, in the case of many proteins, reduces risks of denaturation, etc. as compared to more extreme pH ranges.

In the methods described herein, ligand density on the matrix is selected so that target compound binding is achieved at high and low ionic strength. On a wet basis, the ligand density required to effect such binding is preferably at least about 150 µmols per milliliter of resin and more preferably at least about 175 µmols per milliliter of resin and still more preferably at least about 200 µmols per milliliter of resin. On a dry basis, the ligand density required to effect such binding is preferably at least about 1 mmol per gram dry weight of resin and more preferably at least about 1.33 mmol per gram dry weight of resin. This may permit processing of aqueous media without dilution, concentration, desalting, salt addition or particulate removal. Another advantage contemplated by the use of the resins described herein is that these resins may suffer less fouling than resins previously employed for separating target compounds such as proteins from broths.

Upon separation of the target compound from the resin in the manner described above, the recovered target compound solution can be further treated by conventional methods.

The resin employed in this process can be regenerated by conventional methods. For example, resins employing ligands with functional groups which become positively charged may be regenerated using 0.1M HCl, with or without a polarity reducing agent such as ethanol or ethylene glycol. Likewise, resins employing ligands with functional groups which become negatively charged may be regenerated using 0.1M NaOH, again with or without a polarity reducing agent such as ethanol or ethylene glycol. However, exposure to caustic can result in hydrolysis of CDI matrices and can cause matrix swelling. Cross-linking the cellulose matrix before activation has been used to reduce swelling and improve column flow rates. Cross-linking may also be used with positively ionizable matrices.

When foulant is a problem, pretreatment of aqueous medium by flow through an inexpensive resin such as DEAE at high ionic strength may improve separation. For example, when the target compound is subtilisin, use of pretreatment with a DEAE column with subtilisin samples results in significant depletion of foulants, with more than 99% enzyme activity remaining. Depletion of foulants improves regeneration, resin lifetime, and capacity. This extra step may be especially feasible where the flow through from the pretreatment column can be loaded directly onto the separation systems of the present invention without buffer adjustment.

As noted above, the resin as well as the process conditions (e.g., buffers) selected are relative to the target compound to be purified. For example, the protein subtilisin is unstable below pH 4.5, so buffers below that pH cannot be used. In addition, titrate buffers should be avoided when working with subtilisin in order to avoid $Ca^{2+}$ chelation, since $Ca^{2+}$ stabilizes the enzyme. Additionally, phosphate buffers can precipitate $Ca^{2+}$ and, therefore, such buffers should also be avoided. The preferred working range for subtilisin is pH 5–7. Operation in the range of pH 7–10 may be acceptable for limited periods. Also, with subtilisin recovery methods, buffers with molarities of from 100–200 mM are preferred for the initial pH adjustment required for desorption. Once pH is adjusted, buffer molarity can be reduced by dilution. Acetate buffer (pH 5.2) gave efficient recovery for most hydrophobic positively ionizable matrices. A glycol buffer containing 8% formate, 40% propylene glycol, pH 5.5 eluted subtilisin from all such matrices tested.

Although the resins described herein have particular utility for large scale target compound recovery using simple binding and desorption procedures, the resins and methods described herein may be used for FPLC and HPLC analytical or high value preparative use. In particular, descending salt gradients may be used when the resin has a hydrophobic character and (a) pH shift to the hydrophilic and/or electrostatic (ionic) form followed by an increasing salt gradient or (b) pH gradient elution to further shift away from the pH of the hydrophobic form.

By using a mixture of affinity ligands plus ionizable ligands, the advantages of affinity binding may be coupled with facile desorption by electrostatic repulsion. Binding would be at a pH where the titratable ligand is only electrostatically partially charged or inert and desorption would be by pH change. This is by analogy to Ruann's method [20] and Teichberg's affinity repulsion [21].

Further, the resins and systems of the present invention may be applied to non-chromatography resin systems such as liquid-liquid extractions and polymer/UF systems. Modified phase-separating polymers, such as polyethylene glycol, for liquid-liquid extraction [22,23], modified membranes [24] or soluble polymer-UF methods [13,25] may also employ the systems of the present invention. In such embodiments, the resin and the matrix need not be solid or water insoluble.

EXAMPLES

The following examples are presented to illustrate specific embodiments of the present invention and should not be interpreted as limitations upon the scope of the invention.

Examples I to VI demonstrate methods for preparing activated resins and/or subsequent attachment of representative ligands. These examples are disclosed in U.S. patent application Ser. No. 08/268,178 filed Jun. 29, 1994 as Attorney Docket No. 010055-126 which application is incorporated herein by reference in its entirety.

In these examples, the abbreviations used have the following meanings. If not defined, any abbreviation used below has its generally accepted meaning.

AEBS=p-(2-aminoethyl)benzenesulfonamide;

API=APImidazole=APIMID=1-(3-aminopropyl)imidazole;

AMB=AMBenzimidazole=2-(aminomethyl) benzimidazole;

APM=APMorpholine=1-(3-aminopropyl)morpholine;

2AMP=2AMPyridine=2-(aminomethyl)pyridine;

3AMP=3AMPyridine=3-(aminomethyl)pyridine;

4AMP=4AMPyridine=4-(aminomethyl)pyridine;

APP=(1S, 2S)-(+)-2-aminophenylpropanediol;

CDI=carbonyl diimidazole;

DAH=diaminohexane;

DEAPA=3-diethylaminopropylamine;

DMSO=dimethylsulfoxide;

ECH=epichlorohydrin;

EDC=(1-ethyl-3-(3-dimethylaminopropyl)carbodiimide;

EEDQ=N-ethoxycarbonyl-2-ethoxydihydroquinoline;

g=grams;

HEX=hexylamine=1-hexylamine;

M=molar;

mg=milligrams;

MG1=1-(3-aminopropyl)imidazole-substituted Perloza resin;

MG2=4-(aminomethyl)pyridine-substituted Perloza resin;

MG3=Uncrosslinked resin on Perloza MT 100 Fine (diameter: 80–100 microns; ligand density: 207 μmol caproic acid/mL)

MG3a=Resin on Perloza MT 100 Fine crosslinked with 1% epichlorohydrin (ligand density: 225 μmol/mL)

MG3b=Resin on Perloza MT 100 Medium Perloza (diameter: 100–250 microns; ligand density: 216 μmol/mL)

mL=milliliter mM=millimolar;

mmho=millimho (1 mS—milliSiemens);

mmol=millimoles;

MB=mercaptobenzimidazole;

methimazole=2-mercapto-1-methylimidazole;

MP=4MP=4-mercaptopyridine;

P=Perloza;

PALOL=phenylalaninol

PCC=Perloza CDI aminocaproic acid resin;

PCDI=CDI activated Perloza;

PEA=phenylethylamine;

PPA=phenylpropanolamine;

psi=pounds per square inch rpm=rotations per minute

S=Sepharose;

TRPN=tryptamine.

μL=microliters

Using the above abbreviations, the resins employed in the following examples are generally abbreviated as follows: [Matrix]-[Coupling Method]-[Spacer Arm]/[ionizable Functionality]. For example, "P CDI 4AMPyridine" refers to a Perloza solid support matrix (P) activated with carbonyl diimidazole (CDI) and coupled with a 4-aminomethylpyridine group; "S ECH Methimazole" refers to a Sepharose solid support matrix (S) activated with epichlorohydrin (ECH) and coupled with the 2-mercapto-1-methylimidazole group (Methimazole); and "P CDI DAH Hydroxyphenylacetic acid" refers to a Perloza solid support matrix (P) activated with carbonyl diimidazole (CDI) and coupled through a diaminohexane spacer (DAH) with hydroxyphenylacetic acid. It being understood, of course, that the spacer arm and the ionizable functionalities comprise the ionizable ligand.

EXAMPLE I

Epoxide Activation

Sepharose 6B (50 g) previously washed with 10 volumes of water, was mixed with 47 mL 1M NaOH and 5 mL of epichlorohydrin for 24 hours at 4° C. Epoxide group substitution was determined by methods known in the art to be 1.06 mmol/g. Similar activations gave epoxide group substitutions of 1.28 and 1.02 mmol/g.

EXAMPLE II

Amine Ligand Attachment to Epoxidated Sepharose

Epoxidated Sepharose (10 g; 1.06 mmol/g dry) prepared as described in EXAMPLE I was mixed with a 5 molar excess (i.e., 5 moles of ligand/mole of resin reactive groups) of a ligand selected from AEBS, APP, TRPN solvated with 4 mL DMSO and 2 mL water for 24 hours at 37° C. A 5 molar excess of BEX was mixed likewise with 10 g epoxidated Sepharose (1.28 mmol/g dry). The resulting resins were washed with 10 volumes of 50% DMSO (DMSO:water, 1:1) (tryptamine resin only), 10 volumes of water, 2 volumes of 0.1M HCl and a further 10 volumes of water. Ligand substitution was determined by 0.1M HCl titration to pH 4 to be 0.81 mmol/g for APP Sepharose and 0.99 mmol/g for HEX Sepharose. This represented approximately 80% efficiency of ligand substitution of epoxide groups. Improved ligand densities can be achieved by the procedure set forth in Examples III to VII below.

EXAMPLE III

Allyl Glycidyl Ether Activation

Perloza cellulose (Perloza MT 100 fine beaded cellulose available from Secheza, Czechoslovakia) was washed with 5 volumes of water (MilliQ grade water) and 3 volumes of 0.3M NaOH and suction dried. A 40 g quantity of the matrix was mixed with 12 mL of 99+% allyl glycidyl ether by vigorous shaking. The mixture was left at room temperature for 48 hours with occasional shaking. The activated matrix was washed with 10 volumes of water and suspended in 3 volumes of water. Bromine water (1%) was added slowly over 5 minutes until the mixture no longer decolorized the bromine water. The brominated resin was washed with 10 volumes of water. Allyl group concentration on the resins was determined by the amount of bromine water decolorized. The concentration of reactive bromine groups on the resin (1 g sample suspended in 9 mL water) was determined by substitution with 0.5 g sodium sulfite (4 hours, 60° C.), followed by 0.1M NaOH titration to pH 8.

Allyl Bromide Activation

Perloza cellulose (MT 100 fine) was washed with 5 volumes of water (MilliQ grade) and suction dried. A 10 g quantity of the matrix was mixed with 0.8 mL allyl bromide (redistilled), 0.8 g barium hydroxide octahydrate, 2 mL DMSO and 1 mL water for 48 hours at room temperature. The activated matrix was washed with 5 volumes of a 10% DMSO/90% water mixture, 5 volumes of 0.1M HCl and 10 volumes of water. Allyl group concentration was determined by the bromine water method described above. An independent measure of allyl groups was obtained by mixing 1 g of the activated resin with 3 mL water and 100 μL of 3-mercaptopropionic acid at 60° C. for 4 hours. This derivatized resin was washed with 20 volumes of water, 20 volumes of 0.1M NaOH, 50 volumes of water, 20 volumes of 0.1M HCl and 100 volumes of water and titrated with 0.1M NaOH. This titration method can also be applied to activated matrices described above.

EXAMPLE IV

Thiol Ligand Attachment

A resin (5 g), produced as described in EXAMPLES I or III above, was suspended in 5 mL of 1M phosphate buffer (pH 7) and flushed with nitrogen. A 5 molar excess of a ligand (4MP, methimazole, or MB (dissolved in 5 mL of DMSO) or thiosalicyclic acid) and 0.1 g sodium borohydride were added and the mixture reacted for six hours. Resins produced by the method of EXAMPLE 1 were maintained at room temperature. Resins produced by methods of EXAMPLES III or IV were maintained at 60° C. The resulting thioether resin was washed with 5 volumes of 0.1M HCl, 10 volumes of water, 5 volumes of 0.1M NaOH and 20 volumes of water. A sample (1 g) was titrated with 0.1M HCl to pH 3.5-2.7 (lower end pH for MB ligand). Thiosalicylic acid resins were washed with NaOH, water, HCl and water and titrated with 0.1M NaOH to pH 8.

EXAMPLE V

Hydroxyl (Phenol) Ligand Attachment

The resin (5 g), produced as described in EXAMPLE III, was mixed with a 10 molar excess of hydroxyphenylacetic acid (prepared by dissolving in 2 mL of water and sufficient 1M NaOH to adjust the pH to 11.5). The mixture was reacted for twenty four hours at room temperature. The resin was washed with 5 volumes of 0.1M NaOH, 10 volumes of water, 5 volumes of 0.1M HCl and 20 volumes of water. A sample (1 g) was titrated with 0.1M NaOH to pH 8.

4-hydroxybenzoic acid could also be employed in a similar manner except that the pH is adjusted to pH 11. This compound as well as thiosalicylic acid are useful in preparing ligands suitable for subtilisin recovery.

EXAMPLE VI

CDI Activation and Ligand/Spacer Arm Attachments

Sepharose CL6B and Perloza cellulose were activated with CDI and titrated by methods known in the art. Activation levels between 1.0 and 3.5 mmol/g were obtained using 30 to 80 mg CDI per g Sepharose and 30 to 120 mg CDI per g cellulose.

Amine reagents soluble in dioxane (API, APM, histamine, AMB, 4AMP, 3AMP, 2AMP, DAH, tyramine (prepared from the hydrochloride by dissolving in water, adjusting the pH to 12 with 1M NaOH and freeze-drying) and dibromotyramine (prepared from tyramine hydrochloride by methods known in the art)) were reacted directly with 10 g samples of dioxane solvated CDI activated matrices (1 mL of water was included with the tyramine ligands). A 5 molar excess of amine reagent was used except for DAH which was used in 10 molar excess. Dioxane (5ml) was added and the resin was mixed for 24 hours at room temperature. The resins were washed with 3 volumes of 75% dioxane, 2 volumes of 33% dioxane, 10 volumes of water, 2 volumes of 0.1M HCl and further with 10 volumes of water.

Aminocaproic acid and nitrotyrosine (sodium salt forms) were not soluble in dioxane. Therefore, a 40% solution of sodium aminocaproate was prepared by dissolving 80 g of aminocaproic acid in 64 mL of 10M NaOH and water to a final volume of 200 ml. Dioxane solvated activated cellulose (300 g resin+150 mL dioxane) and Sepharose (100 g resin+ 50 mL dioxane) were mixed with 80 mL and 30 mL respectively of the sodium aminocaproate solution for 24 hours at room temperature. The aminocaproic resins were washed with 2 volumes of 66% dioxane, 2 volumes of 33% dioxane and 20 volumes of water. Similarly, nitrotyrosine was dissolved in water and 3M NaOH to produce a 15% solution at pH 11.3. Activated cellulose (10 g) solvated with 50% dioxane was mixed with 13 mL of nitrotyrosine solution for 24 hours at room temperature.

EXAMPLE VII

Ligand Attachment by Amide Bonds (Condensation Reactions)

(a) 100% coupling of amine ligands to resin carboxyl groups:

A 5 molar excess of ligand (4-AMP, 3-AMP, dimethylaminopropylamine or API) was adjusted to pH 4.7 with 6M HCl and mixed with aminocaproic resin (1.55 mmoL/g). The pH was adjusted to 4.7 with 1M HCl or NaOH as appropriate and mixed with a 3M excess of water soluble carbodiimide (EDC, 50% solution in water). The pH was maintained at 4.7 for 1 hour with 1M HCl or NaOH, as appropriate, and mixed for a further 10 hours without adjustment at room temperature. A further 1 molar excess of EDC was applied in the same manner as before (1 +10 hours). The resin was washed with 10 volumes of water, 2 volumes of 0.1M HCl and 10 volumes of water. Ethanolamine was coupled to nitrotyrosine cellulose by the same method. No residual carboxyl groups could be detected on these resins by titration methods sensitive to 20 μmol/g.

(b) Partial (50–80%) coupling of amino ligands to resin carboxyl groups:

A 1.5 molar excess of a ligand selected from APP, PPA, PEA or PALOL was adjusted to pH 4.7 with 6M HCl and mixed with aminocaproic resin. The pH was maintained at pH 4.7 with 1M HCl or NaOH as appropriate and a 1.5M excess of EDC was added. The pH was maintained at pH 4.7 for 1 hour followed by 10 hours mixing without pH adjustment, as described previously. The resin was washed as described previously and the content of residual carboxyl groups determined by titration.

(c) 100% coupling of carboxyl ligands to diaminohexane resins (1.24 mmol/g):

This method is similar to that of (a) above but the ligand (4-hydroxyphenylacetic acid, 3-chloro-4-hydroxyphenylacetic acid or 3-nitro-4-hydroxybenzoic acid) pH was adjusted with 1M NaOH. The pH was maintained at 5, diaminohexane cellulose was used and a 0.1M NaOH wash replaced the HCl wash. For dichlorosalicylic acid, a sodium salt was prepared by 1M NaOH addition to a suspension of the acid (0.3 g) in water until pH was stable at 7 and freeze-drying. The salt was dissolved in 10 mL DMSO and mixed with ethoxycarbonylethoxydihydroquinoline (EEDQ), (0.5 g dissolved in 5 mL of ethanol) and 50% DMSO solvated diaminohexane cellulose. The mixture was shaken for 6 hours at temperature. A further 0.5 g EEDQ was introduced and the reaction continued for 18 hours. The resin was washed with 5 volumes of DMSO, 2 volumes of 50% DMSO, 10 volumes 0.1M NaOH and 10 volumes of water. Coupling of resin amino groups by these methods was only 80 to 90% complete. Residual amino groups were blocked by methods known in the art, e.g. acetylation.

EXAMPLE VIII

Methods for Chymosin Purification

Resins produced as described in EXAMPLES II, III (using 4MP) and VI (using 2AMP, 3AMP, and 4AMP) were packed in disposable columns and equilibrated with load buffer A (pH 5.5: 10 mM titrate±0.5M NaCl). Chymosin samples were adjusted to the same pH and ionic strength and applied to the column. Unbound contaminants were washed out with load buffer at both ionic strengths listed in this example using buffers A and B (30 column volumes each). The resins were eluted with 50 mM KCl adjusted to pH 2 with HCl. The presence of chymosin activity was assayed qualitatively by incubating a 200 µl sample with 5 mL fresh whole milk at 37° C. for up to 1 hour. Activity was only detected in the elution fraction.

Resins produced as described in EXAMPLE VI (PCC) and EXAMPLE VIIb were packed as above but equilibrated with a load buffer B (pH 4.4 and 10 mM citrate±0.5M NaCl). Chymosin samples were adjusted to these load conditions and applied to the column. Contaminants were washed out with load buffer B as before. The resins were eluted with 20 mM citrate pH 6.2. Chymosin activity was only detected in the elution fraction.

In contrast to the results of this example, resins prepared from a similar matrix and employing DEAPA and APIMD did not bind chymosin at high ionic strengths because the balance of the hydrophobicity/hydrophilicity and charge was not suitable. These results clearly demonstrate the need for suitable selection of the ionizable functionality, spacer arm and solid support matrix to effect both binding at one pH and desorption at another pH.

EXAMPLE IX

Resin Capacities for Chymosin

Capacity testing was conducted by batch operations using purified recombinant chymosin. The chymosin was dialyzed and lyophilized prior to use. Load buffers used were those containing 0.5M NaCl described in EXAMPLE VIII. The resin was equilibrated with load buffer (5 volumes) and suction dried. One sample of this resin (2–4 g) was weighed into a 10 mL measuring cylinder, suspended in load buffer and left to settle for 48 hours (to determine the resin weight: volume ratio). Another sample of the resin (0.1–0.15 g) was weighed into a 25 mL vial and mixed with 25 mg of chymosin dissolved in 10 mL load buffer, for 1 hour at 4° C. on a rotating wheel. The contents of the vial were quantitatively transferred to a Pierce disposable 2 mL minicolumn and washed with 10 mL of load buffer. The resin was eluted with the appropriate buffer (as described in EXAMPLE VIII) into a 10 mL volumetric flask. The elution was analyzed by ultraviolet absorbance at 280 nanometers and protein assay (using the bicinchoninic acid assay). Capacity data expressed in mg protein/mL of resin is shown in Table 2 below:

TABLE 2

| RESIN | CAPACITY (mg protein per ml resin) |
|---|---|
| S ECH AMP | 31 |
| S ECH HEX | 22 |
| P CDI AMINOCAPROIC ACID (100% SUBSTITUTION) | 68 |
| P CDI CAPROIC ACID-APP (67% SUBSTITUTION) | 71 |
| P CDI CAPROIC ACID-PPA (59% SUBSTITUTION) | 68 |
| P CDI CAPROIC ACID-PALOL (78% SUBSTITUTION) | 80 |

% substitution refers to the percent of caproic acid or aminocaproic acid carboxyl groups substituted with the recited ionizable functional group.

EXAMPLE X

Titration of Hydrophobic Positively Ionizable Resins

A sample of the resin (1 g; wet weight) to be titrated was washed with 0.1M NaOH and then rinsed with water. The sample was then suspended in 9 mL of 500 mM NaCl solution (or as noted in Table 3) and titrated with 0.1 N HCl. Titration figures were corrected for dilution effects by subtracting titration values obtained for a underivatized Perloza control. The titration data is shown in Table 3.

TABLE 3

Titration Data

| Resin | Resin pKa | pH Uncharged Form Starts to Titrate | pH 90% Charged |
|---|---|---|---|
| PCC DEAPA | 9.3 | 10.5 | 8.4 |
| P CDI APMorpholine | 7.1 | 8.9 | 6.2 |
| PCC APImidazole | 6.25 | 8.0 | 4.8 |
| P CDI AMBenzimidazole | 4.8 | 6.75 | 4.0 |
| P CDI 2AMPyridine | 4.1 | 6.1 | 3.0 |
| P CDI 4AMPyridine | 4.7 | 7.2 | 3.7 |
| PCC 3AMPyridine | 4.2 | 7.0 | 3.3 |
| PCC API (10 mM NaCl) | 5.0 | 8.0 | 3.6 |
| P CDI APM (10 mM NaCl) | 5.8 | 8.05 | 4.8 |
| P CDI AMB (10 mM NaCl) | 3.6 | 6.45 | 3.0* |
| S ECH Methimazole | 5.6 | 7.6 | 4.5 |
| S ECH 4-Mercaptopyridine | 5.35 | 7.6 | 4.2 |
| S ECH Mercaptobenzimidazole | 4.2 | 6.5–7.0 | 3.1 |

*At low pH values, greater error is likely due to acid dilution.

EXAMPLE XI

Titration of Hydrophobic Negatively Ionizable Resins

A sample of the resin (1 g) in 0.5M NaCl was adjusted to pH 12 with 1M NaOH and then titrated to pH 3 with 0.1M HCl. Titration figures were corrected for dilution effects by subtracting titration values obtained for a underivatized Perloza control. The titration data are shown in Table 4.

TABLE 4

Titration Data

| Resin | Resin pKa | pH Uncharged Form Starts to Titrate | pH 90% Charged |
|---|---|---|---|
| P CDI DAH Nitrohyroxyphenylacetic Acid | 6.4 | 4 | 7.5 |
| P CDI Nitrotyrosine/ethanolamine | 7.2 | 5 | 9.0 |
| P CDI DAH Dichlorosalicylic Acid | 7.2 | 5 | 9.3 |
| P CDI Dibromotyramine | 7.7 | 5 | 9.3 |
| P CDI DAH Chlorohydroxyphenyl-acetic Acid | 9.8 | 6.5 | 10.8 |
| P CDI DAH Hydroxyphenylacetic Acid | 10.7 | 7.5 | 11.2 |
| P CDI Tyramine | 10.7 | 7.5 | 11.2 |
| PCC | 5.2 | 3.0 | 6.5 |
| PCC (10 mM NaCl) | 6.1 | 3.3 | 7.5 |

The data in Tables 3 and 4 show the pH range in which representative resins having an ionizable functionality are converted from a electrostatically uncharged state to an electrostatically charged state. This data illustrate that one skilled in the art may prepare and select various resins having different ionization profiles thereby permitting the use of a resin which is compatible with the target compound to be recovered.

EXAMPLE XII

Batch Binding Capacities for Subtilisin from Crude Fermentation Broth of CDI Activated Perloza Cellulose Containing Amino Caproic Acid Ligands Perzola cellulose was activated with CDI and the amino caproic acid ligands were attached in a manner similar to that described in Example VI above. Three variations of the resin were prepared as follows:

MG3=Uncrosslinked resin on Perloza MT 100 Fine (diameter: 80–100 microns; ligand density: 207 μmol caproic acid/mL)

MG3a=Resin on Perloza MT 100 Fine crosslinked with 1% epichlorohydrin (ligand density: 225 μmol/mL)

MG3b=Resin on Perloza MT 100 Medium Perloza (diameter: 100–250 microns; ligand density: 216 μmol/mL)

Capacity testing was conducted by batch operation using similar Bacillus subtilis fermentation broths. Capacity testing using MG3 resin employed a variant of Bacillus subtilis as described in U.S. patent application Ser. No. 08/137,240 filed on Oct. 14, 1993 and incorporated herein by reference. Capacity testing using MG3a and MG3b resins employed commercially available subtilisin (PURAFECT™ subtilisin available from Genencor International, Inc., South San Francisco, Calif., U.S.A.). In each case, subtilisin was the target compound. In each case, the broth also contained a large variety of extraneous compounds, including proteins. The conductivity of the broth was 16 mmho. Crude cell separation was performed by centrifuging the broth at 45,000 rpm in a Sorvall refrigerated centrifuge for 20 minutes, and using only the supernatant.

4.0 g of the wet resin was equilibrated with a 50 mM sodium acetate buffer at pH 5.2 up to a volume of 10 mL. The settled volume of the resin was recorded prior to the beginning of the experiment.

50 mL of broth was adjusted to pH 5.2 with glacial acetic acid. This amount of broth represents a large excess of protein concentration over resin capacity and ensures that the protein concentration on the resin is at its practical maximum. At time zero, 10 mL of buffer and resin were added to the broth. An additional 1 mL of water was added to rinse the test tube. The mixture was stirred in a beaker of known weight under refrigeration for over 3 hours. At that time, the supernatant was filtered through a buchner funnel containing Whatman 47 filter paper. The supernatant was weighed and a 0.5 mL sample was collected.

The resin was rinsed, placed back into the beaker and contacted with less than 100 mL of 50 mM acetate buffer, pH 5.2, to remove non-selective binding components. The wash step lasted 25–30 minutes. This solution was again filtered and a sample collected. Samples of binding and wash fractions were analyzed for activity. Table 5 below illustrates that after washing, all resins had very high capacity for subtilisin in broth that was minimally treated before loading.

TABLE 5

| RESIN | Subtilisin Capacity (mg/mL) | Total Protein Capacity (mg/mL) |
|---|---|---|
| MG3 | 41.0–59.08[a] | 69.06–118[a] |
| MG3a | 48.08 | — |
| MG3b | 46.25 | — |

[a]two runs were conducted for this resin.

EXAMPLE XIII

Recovery of Subtilisin from Crude Fermentation Broth using CDI Activated Perloza Cellulose Containing Amino Caproic Acid Ligands in a Radial Flow Column The MG3a crosslinked resin described in Example XII was prepared as described in Example VI.

A 50 mL radial flow chromatography column (Sepragen Corp., San Leandro, Calif.) was packed with this resin and used to effect recovery of subtilisin from a Bacillus subtilis fermentation broth as described below:

Broth Treatment

The whole broth was centrifuged for 30 minutes in a chilled Sorvall centrifuge at 4,500 rpm. The conductivity of the centrate was adjusted to pH 5.2 using glacial acetic acid. No dilutions were made. The conductivity of the broth was 20 mmho. Subtilisin was the target compound and the broth also contained a large variety of extraneous compounds, including proteins.

Buffers

Equilibration Buffer: 100 mM Sodium Acetate, pH 5.2,+ NaCl to 20 mmho

Wash Buffer: 20 mM Sodium Acetate, pH 5.2,+NaCl to 20 mmho

Elution Buffer: 100 mM Glycine, 40% propylene glycol, 8% sodium formate, pH 9, 35 mmho Regeneration Buffer: 0.1M NaOH 460 mL of centrifuged broth was loaded onto the column at pH 5.2 and a conductivity of 20 mmho. The column was purposely overloaded in order to estimate dynamic capacity, so excess enzyme was expected in the flow-through and wash fractions. The flow rate was 10 mL/minute. The column was washed at 15 mL/minute until the ultraviolet (UV) absorbance fell below 15% of full scale. This required 61 column volumes of wash buffer. The column was eluted over 16 column volumes at 5 mL/minute. After the wash, the subtilisin capacity of the resin was 31 mg/mL. The pressure throughout the run was below 4 psi.

The protein was eluted by increasing the pH and the conductivity using the above elution buffer. 94% of the bound protein was recovered. 0.5 or 1 column volume elution fractions were collected, and the concentration of protein (subtilisin) per collected fraction is illustrated in FIG. 8. The maximum fraction concentration was 17.4 mg/mL and 90% of the recovered protein eluted within 3 column volumes.

This process demonstrates a simple and high capacity capture of subtilisin from a complex fermentation broth with minimal broth pretreatment. Quantitative recovery in a narrow, concentrated elution peak is also possible with this process.

By following the procedures set forth above with the modification of loading less protein and using a shorter wash step, this compound can be recovered with a high overall yield. The use of propylene glycol in the elution buffer is helpful, but not necessary to achieve complete elution. This procedure may also be easily modified to allow the recovery of other target compounds.

It will be apparent to one of ordinary skill in the art that various changes and modifications of an obvious nature may be made without departing from the spirit of the invention, and all such modifications are considered to fall within the scope of the invention, as set forth in the following claims.

What is claimed is:

1. A resin for binding a target compound which comprises a solid support matrix, selected ionizable ligands or mixtures of selected ionizable ligands covalently attached to the solid support matrix wherein the ionizable ligand comprises a spacer arm and at least one ionizable functionality which functionality is bound to the matrix through the spacer arm, wherein the density of the ionizable ligands on the solid support matrix is greater than the smaller of at least about 150 µmol per milliliter of resin and at least 1 mmol per gram dry weight of resin, the ionizable ligand being selected relative to the solid support matrix and the target compound such that the hydrophobic character of the resin is sufficient to bind at least 50% of the target compound in an aqueous medium at high and low ionic strength at a first pH and is further selected relative to the solid support matrix such that the hydrophilic and/or electrostatic character of the resin at a second pH is sufficient to desorb the bound compound at said second pH, and the ionizable functionality being either further electrostatically charged or charged at a different polarity at the pH the target compound is desorbed from the resin as compared to the charge at the pH of target compound binding to the resin.

2. The resin according to claim 1 wherein said resin optionally comprises selected non-ionizable ligands covalently attached to the solid support matrix and further wherein the percentage of non-ionizable ligands based on the total of ionizable and non-ionizable ligands ranges from about 0 to 80% the non-ionizable ligand being selected relative to the ionizable ligand and the solid support matrix such that the hydrophobic character of the resin is sufficient to bind at least 50% of the target compound in an aqueous medium at high and low ionic strength at a first pH and is further selected relative to the solid support matrix such that the hydrophilic and/or electrostatic character of the resin at a second pH is sufficient to desorb the bound compound at said second pH.

3. The resin according to claim 1 wherein the electrostatic charge on the resin at the pH of compound desorption from the resin is of the same polarity as the net electrostatic charge on the target compound at this pH.

4. The resin according to claim 1 wherein the electrostatic charge on the resin at the pH of compound desorption from the resin is of opposite polarity from the net electrostatic charge on the target compound at this pH.

5. The resin according to claim 1 wherein said ionizable functional group is selected from the group consisting of carboxyl, amino and phenolic groups.

6. The resin according to claim 2 wherein the percentage of non-ionizable ligands attached to the solid support matrix based on the total of ionizable and non-ionizable ligands ranges from greater than 0% to about 40%.

7. The resin according to claim 1 wherein the solid support matrix is cross-linked.

8. The resin according to claim 1 wherein the solid support matrix is non-ionizable.

9. The resin according to claim 1 wherein the solid support matrix comprises ionizable functionality within its backbone.

10. The resin according to claim 1 wherein said target compound is a protein or peptide.

11. The resin according to claim 10 wherein said protein or peptide is selected from the group consisting of chymosin and subtilisin.

12. The resin according to claim 1 wherein the density of ligand is at least about 150 µmol per milliliter of resin.

13. The resin according to claim 1 wherein the density of ligand is at least 1 mmol per gram dry weight of resin.

14. A method for separating a target compound from an aqueous medium comprising the target compound which method comprises contacting the medium with a resin according to claim 1 under conditions suitable for binding at least 50% of the target compound to the resin, including adjusting the pH of the medium.

15. The method according to claim 14 wherein said target compound is a protein or peptide.

16. The method according to claim 15 wherein said protein or peptide is selected from the group consisting of chymosin and subtilisin.

17. A method for binding and recovering a target compound from an aqueous medium comprising the target compound which method comprises:

a) contacting the medium with a resin according to claim 1 under conditions suitable for binding at least 50% of the target compound to the resin;

b) separating the resin containing the bound target compound from the other components of the medium to produce a resin-compound complex; and c) desorbing the bound target compound from the complex by contacting the complex with an chant having a pH sufficiently different from the pH of the medium recited in a) above such that the target compound desorbs from the resin.

18. The method according to claim 17 wherein said target compound is a protein or peptide.

19. The method according to claim 18 wherein said protein or peptide is selected from the group consisting of chymosin and subtilisin.

20. The method according to claim 17 wherein the aqueous medium is contacted with the resin in a stirred batch process.

21. The method according to claim 17 wherein the aqueous medium is contacted with the resin in a chromatography column.

22. The method according to claim 21 wherein the column is a radial flow column.

23. The method according to claim 21 wherein the column is a fluidized expanded bed.

24. The method according to claim 17 wherein the density of ligand is at least about 150 μmol per milliliter of resin.

25. The method according to claim 17 wherein the density of ligand is at least 1 mmol per gram dry weight of resin.

26. A resin having ionizable functional groups pendant to a solid support matrix which resin comprise:

a solid support matrix; and an ionizable ligand which comprises an ionizable functionality and a spacer arm which covalently attaches the ionizable functionality to the solid support matrix wherein said ionizable functionality is derived from a compound selected from the group consisting of 4-(aminomethyl)pyridine, 3-(aminomethyl)pyridine, 2-(aminomethyl)pyridine, 1-(3-aminopropyl)-imidazole, 2-(aminomethyl)-benzimidazole, 4-(3-aminopropyl)morpholine, halotryamines having from 1 to 2 halo groups selected from the group consisting of fluoro, chloro, bromo and iodo, 4-aminobutyric acid, (1S, 2S)-(+)-2-amino-1-phenyl-1,3-propanediol, phenylethylamine, phenylalaninol, 4-(2-aminoethyl)benzenesulfonamide, DL-β-hydroxyphenylethylamine, thiosalicylic acid, 2-mercapto-1-methylimidazole, 2-mercaptobenzimidazole, 4-mercaptoethylpyridine, 2-mercaptoethylpyridine, 4-mercaptobutyric acid, 5-mercaptovaleric acid, 6-mercaptohexanoic acid, 4-hydroxythiophenol, 4-hydroxybenzoic acid, 4-hydroxyphenylacetic acid, 3-chlorohydroxyphenylacetic acid, 3,5-dichlorosalicylic acid, 4-hydroxy-3-nitrobenzoic acid, 3-nitrotyrosine, halotyrosines having from 1 to 2 halo groups selected from the group consisting of fluoro, chloro, bromo and iodo, and para-hydroxybenzoic acid hydrazide.

27. The resin according to claim 26 wherein said ionizable functionality is derived from a compound selected from the group consisting of 4-(aminomethyl)pyridine, 3-(aminomethyl)pyridine, 2-(aminomethyl)pyridine, 1-(3-aminopropyl)-imidazole, 2-(aminomethyl)-benzimidazole, 4-(3-aminopropyl)morpholine.

28. A resin having ionizable functional groups pendant to a solid support matrix which resin comprises:

a solid support matrix; and ionizable ligand pendant to said support at a density greater than the smaller of either at least about 150 μmol per milliliter of resin or 1 mmol per gram dry weight of resin which comprises an ionizable functionality and a spacer arm which covalently attaches the ionizable functionality to the solid support matrix wherein said ionizable functionality is derived from a compound selected from the group consisting of aminocaproic acid, 2-mercaptopyridine, 4-mercaptopyridine, aminoethylbenzenesulfonamide, tyramine, tyrosine, and histidine.

* * * * *